United States Patent
McCurdy et al.

(10) Patent No.: US 11,513,061 B2
(45) Date of Patent: Nov. 29, 2022

(54) SYSTEM FOR NONDESTRUCTIVE SPECTROSCOPIC ANALYSIS OF BIOLOGIC SPECIMENS

(71) Applicant: UNIVERSITY OF MARYLAND, BALTIMORE, Baltimore, MD (US)

(72) Inventors: Michael T. McCurdy, Elkridge, MD (US); Rajagopal Srinivasan, Baltimore, MD (US)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 0 days.

(21) Appl. No.: 17/254,958

(22) PCT Filed: Jul. 1, 2019

(86) PCT No.: PCT/US2019/040081
§ 371 (c)(1),
(2) Date: Dec. 22, 2020

(87) PCT Pub. No.: WO2020/006549
PCT Pub. Date: Jan. 2, 2020

(65) Prior Publication Data
US 2021/0172864 A1   Jun. 10, 2021

Related U.S. Application Data

(60) Provisional application No. 62/691,771, filed on Jun. 29, 2018.

(51) Int. Cl.
| | | |
|---|---|---|
| *G01N 33/48* | (2006.01) | |
| *G01N 21/25* | (2006.01) | |
| *G01N 21/33* | (2006.01) | |
| *G01N 21/3577* | (2014.01) | |
| *G01N 21/64* | (2006.01) | |

(Continued)

(52) U.S. Cl.
CPC .......... *G01N 21/255* (2013.01); *G01N 21/33* (2013.01); *G01N 21/3577* (2013.01);
(Continued)

(58) Field of Classification Search
CPC .... G01N 33/49; G01N 15/05; G01N 15/1434; A61B 5/14532; A61B 5/1455
USPC .......................................................... 356/39
See application file for complete search history.

(56) References Cited

U.S. PATENT DOCUMENTS

| | | |
|---|---|---|
| 4,684,245 A | 8/1987 | Goldring |
| 5,341,805 A | 8/1994 | Stavridi et al. |

(Continued)

FOREIGN PATENT DOCUMENTS

| | | |
|---|---|---|
| CN | 101893542 A | 11/2010 |
| JP | 62226057 A | 10/1987 |

(Continued)

OTHER PUBLICATIONS

PCT Collaborative Search and Examination Report for related application PCT/US2019/040081 filed Jul. 1, 2019, dated Sep. 16, 2019. (50 pages).

*Primary Examiner* — Md M Rahman
(74) *Attorney, Agent, or Firm* — Tristan A. Fuierer; Casimir Jones, S.C.

(57) ABSTRACT

A device for monitoring at least one parameter of a fluid specimen obtained from a patient. The device has a fluid conduit holder comprising a clamp configured to position a fluid conduit, which holds the fluid specimen obtained from the patient, in a position for optical analysis, and an optical analyzer having a light source and a light detector. The optical analyzer is configured to expose the fluid specimen contained within the fluid conduit to an illuminant and measure light received at the detector. The device has an optical alignment mechanism mechanically coupling the light source, the clamp, and the light detector together, and configured to align at least the light detector with the fluid conduit at the position for optical analysis.

20 Claims, 14 Drawing Sheets

(51) Int. Cl.
  *G01N 33/49*   (2006.01)
  *G01N 33/493*  (2006.01)
  *A61B 5/1459*   (2006.01)
  *G01N 21/03*    (2006.01)

(52) U.S. Cl.
  CPC ......... *G01N 21/6486* (2013.01); *G01N 33/49* (2013.01); *G01N 33/493* (2013.01); *A61B 5/1459* (2013.01); *G01N 2021/0364* (2013.01); *G01N 2021/0367* (2013.01); *G01N 2201/062* (2013.01)

(56) References Cited

U.S. PATENT DOCUMENTS

| | | | |
|---|---|---|---|
| 5,456,253 | A | 10/1995 | Steuer et al. |
| 5,817,007 | A | 10/1998 | Fodgaard et al. |
| 5,963,335 | A | 10/1999 | Boutelle |
| 6,043,871 | A | 3/2000 | Solen et al. |
| 6,982,431 | B2 | 1/2006 | Modlin et al. |
| 7,452,507 | B2 | 11/2008 | Renzi et al. |
| 7,608,042 | B2 | 10/2009 | Goldberger et al. |
| 2002/0167667 | A1 | 11/2002 | Samsoondar et al. |
| 2006/0166302 | A1 | 7/2006 | Clarke et al. |
| 2007/0041877 | A1 | 2/2007 | Maurer et al. |
| 2009/0293588 | A1 | 12/2009 | Riley et al. |
| 2012/0019823 | A1 | 1/2012 | Flank et al. |

FOREIGN PATENT DOCUMENTS

| | | |
|---|---|---|
| JP | 62142348 U | 8/1994 |
| JP | 11037931 A | 12/1999 |
| JP | H1137930 A | 12/1999 |
| WO | 2014118601 A1 | 8/2014 |

SYSTEM FOR NONDESTRUCTIVE SPECTROSCOPIC ANALYSIS OF BIOLOGIC SPECIMENS

CROSS REFERENCE TO RELATED APPLICATIONS

This application is filed under the provisions of 35 U.S.C. § 371 and claims priority to International Patent Application No. PCT/US2019/040881 filed on Jul. 1, 2019 which in turn claims priority to U.S. Provisional Application No. 62/691,771, filed on Jun. 29, 2018, the contents of all applications above are hereby incorporated by reference herein for all purposes.

BACKGROUND OF THE INVENTION

Field of Invention

The present invention is related to a system for measuring biologic specimens taken from a patient.

Discussion of the Background

A longstanding paradigm in medicine involves obtaining biologic specimens, such as blood or urine from patients, and transporting the specimens in specialized containers to a laboratory for analysis. This paradigm has remained largely unchallenged for decades despite numerous technological advances occurring during that time.

Critically-ill patients (e.g., those with upper gastrointestinal hemorrhage or multi-system traumatic injury), for example, require frequent blood draws to closely monitor clinical parameters such as hemoglobin concentration. Unfortunately, frequent blood draws result in iatrogenic anemia. Patients may require blood product transfusion just to replace the volume of blood lost to lab testing, let alone what they might lose from illness. Routine testing harms the hemorrhaging patient in a manner identical to the presenting illness.

Very few tests in isolation are capable of answering clinical questions accurately or meaningfully. For instance, hemoglobin levels may remain normal even as a patient exsanguinates if the bleeding is sufficiently brisk. Even highly specific "gold standard" blood tests (such as serum troponin) can be misleading or uninterpretable in the absence of other test results or clinical context. Typical clinical questions (e.g., is this patient suffering from septic shock and/or cardiogenic shock) ultimately require a subjective interpretation of a large number of such lab tests, many of which will be spurious simply by chance and often prompt further blood removal for analysis. Although a useful paradigm when introduced, "blood testing" is, at best, a rational method of augmenting clinical judgment; at worst, it is an imperfect and harmful aspect of medical care that muddies the diagnostic waters.

Laboratory testing requires specialized, expensive equipment that may include a variety of blood test tubes, as well as methods to physically transport the biologic specimen to the laboratory. Medical tubes today are specialized, making their acquisition cost expensive, and the cost of medical waste disposal is expensive. Many lab tests rely on economies of scale which result in transport-related problems, delays, and expenses. Even point-of-care, drop-of-blood testing (e.g., iStat), requires a supply of consumables such as cartridges that limit use in resource-limited settings and far-forward battlefield care. Furthermore, extracting patients' blood exposes medical workers to sharp needles with potentially biohazardous fluid.

Pulse oximetry is a remarkable advancement, replacing the traditional arterial blood gas measurement with a rapid point-of-care noninvasive continuous monitoring technique to immediately detect dangerous drops in arterial oxygenation. Pulse oximetry accomplishes this using light passing through perfused tissue and a filtering technique to specifically identify the arterial signal components, which fluctuate in a periodic, pulsatile manner. This technology revolutionized the safety of anesthesia after widespread adoption in the 1980s. Unfortunately, many critically ill patients nowadays cannot be reliably monitored using pulse oximetry because blood flow characteristics essential for it to properly function may be absent. For example, patients presenting in a shock state, such as from sepsis, may have poor skin and extremity perfusion, and patients with left ventricular assist devices may not have pulsatile arterial blood flow. For these patients, the clinician must resort to serial blood gas sampling, which involves inherent risks and delays associated with blood draw, transport, analysis, and reporting of results before being able to intervene appropriately.

Clinicians routinely are forced to await important laboratory results needed to optimally manage a critically ill patient whose survival may be determined by receiving the proper care within minutes (e.g., hemoglobin, lactate), make a disposition decision for an emergency department patient whose subsequent care may be dictated by the results of certain tests (e.g., troponin, D-dimer), or determine the proper medication initiation or order a diagnostic test for a clinic patient who normally may otherwise have to wait a week before being notified of laboratory results (e.g., creatinine, prostate-specific antigen [PSA]). Such medical care delays are not simply inconveniences but are, in fact, serious obstacles that hinder the health of both individual patients and the population at large; moreover, these delays may be preventable.

The following references describing the state of the art are herein incorporated by reference in their entirety:

U.S. Pat. No. 7,608,042 describes apparatuses and methods for the automated measurement of blood analytes and blood parameters for bedside monitoring of patient blood chemistry. Particularly, the current invention discloses a programmable system that can automatically draw blood samples at a suitable programmable time frequency (or at predetermined timing), can automatically analyze the drawn blood samples and immediately measure and display blood parameters such as glucose levels, hematocrit levels, hemoglobin blood oxygen saturation, blood gases, lactate or any other blood parameter.

U.S. Pat. No. 8,489,165 describes a device for measuring blood and physiological characteristics by passing light through human tissue that is configured for deployment on a human finger. The '165 device includes a lower finger-trough configured in the main housing of the device; a hingedly attached closeable lid that has an upper finger-trough configured for deployment of at least one finger stabilizing element, the lid being latch-able in a closed position; a finger stabilizing element made of a material having flexibly soft malleable characteristics so as to sealingly engage the top of the finger; a light source that is deployed in the sloped end wall of the lower finger-trough adjacent to the lower portion of the fingertip; and an end cap the is deployable on the open end of the device when the lid is in the closed position, which enables calibration of the device with a minimum of light wave "noise" from ambient light.

U.S. Pat. No. 4,883,764 describes a blood test strip including a support member having an upper surface and lower surface. A separating member is disposed on the upper surface of the support member, and includes an upstream end and a downstream end. A recipient member is disposed on the upper surface of the support member in a side by side relation to the separating member. The recipient member of the '764 patent includes an upstream end disposed in an adjacent, non-interwoven relation to the downstream end of the separating member to define an incision therebetween.

U.S. Pat. No. 6,493,568 describes a patient interface system integral with a critical care bed for allowing the acquisition, analysis, display, and conveyance of patient-related data from a variety of transducers (including a blood-oxygen transducer connected to the patient). The '568 system is adapted to recognize and interpret each type of signal being received, despite the type and/or make of the particular transducers. The system is also adapted to simultaneously display data traces and representative readings from a variety of transducers simultaneously on a single screen detachably mounted to the bed.

U.S. Pat. No. 5,596,986 describes a backscatter type non-invasive blood oximeter which utilizes a coherent, polarized and tunable monochromatic light source to measure parameters related to blood oxygen content. A microprocessor of the '986 patent calculates information related to blood oxygen content from the sensed information and a display system displays the blood oxygen content.

U.S. Pat. No. 8,333,715 describes a blood glucose sampling device which includes a sensor cartridge having a plurality of blades oriented in a common direction of rotation about a central point. Each blade includes a test strip having a test region defined radially from the central point at a proximal end and a capillary aligned with a distal end of the test region and extending to an outer edge of the blade. Each blade also includes a cleaning element positioned adjacent to the test strip. A lancet is affixed to a lancet cartridge and aligned with the capillary formed in the test strip. A housing removably encloses the cartridges and includes an outer grip that surrounds a circumference of the housing and is shaped to fit between a thumb and finger. A test passage formed in the outer grip through which the test strip and lancet are positioned.

U.S. Pat. No. 10,209,178 describes a biophotonic device for the point-of-care, real-time, noninvasive determination of parameters with diagnostic relevance. The device includes an optical system to characterize an element of body fluid. The device also includes a modular probe for puncturing skin to obtain a sample, and the probe is attached with a pressure or magnetic attachment system having a correct polarity.

SUMMARY OF THE INVENTION

According to one embodiment, there is provided a device for monitoring at least one parameter of a fluid specimen obtained from a patient. The device has a fluid conduit holder comprising a clamp configured to position a fluid conduit, which holds the fluid specimen obtained from the patient, in a position for optical analysis, and an optical analyzer having a light source and a light detector. The optical analyzer is configured to expose the fluid specimen contained within the fluid conduit to an illuminant and measure a spectrum of light received at the detector. The device has an optical alignment mechanism mechanically coupling the light source, the clamp, and the light detector together, and configured to align at least the light detector with the fluid conduit at the position for optical analysis.

According to one embodiment, there is provided a method for monitoring at least one parameter of a fluid specimen obtained from a patient using the device noted above. In this method, a fluid specimen is received from a patient in a fluid conduit defining a sterile space contiguous with a patient's body; the fluid specimen in the fluid conduit is exposed to incident light; and light transmitted through the fluid conduit and the fluid specimen is measured.

It is to be understood that both the foregoing general description of the invention and the following detailed description are exemplary, but are not restrictive of the invention.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
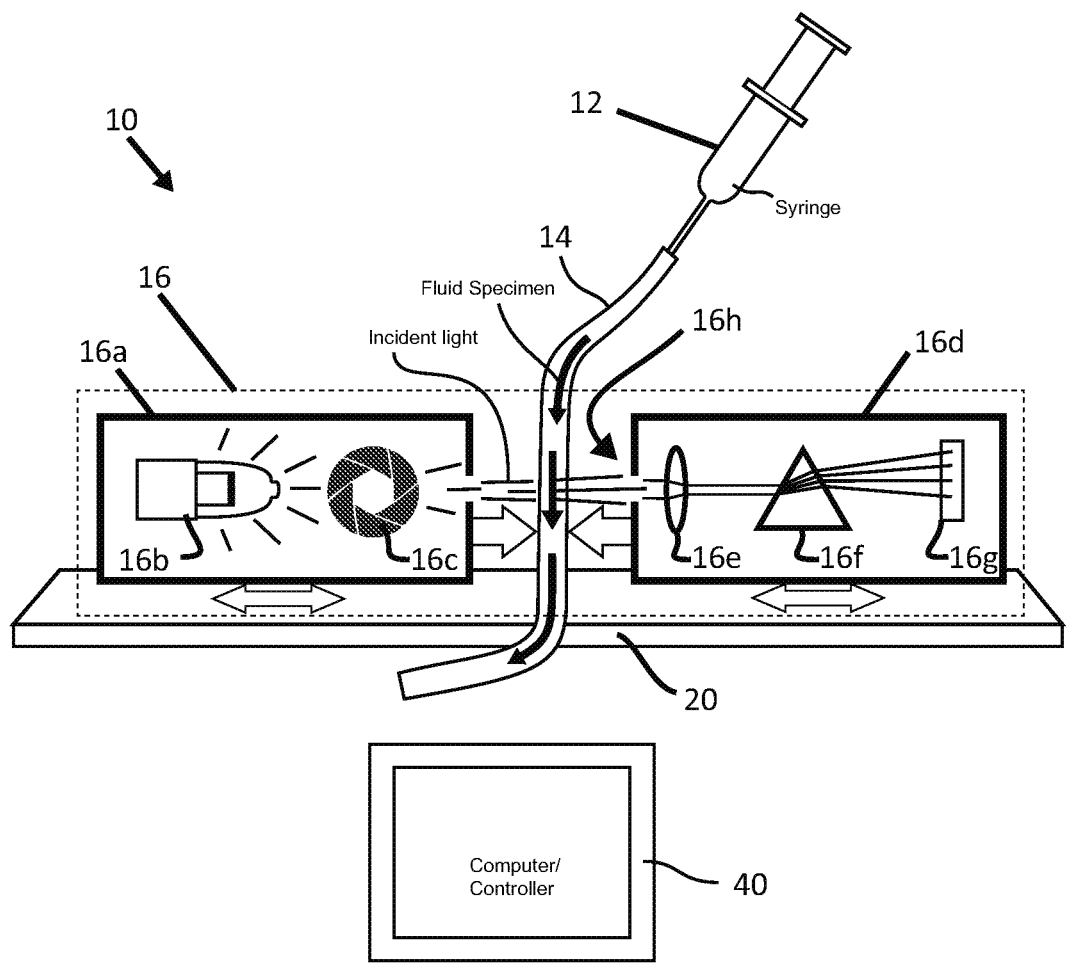
FIG. 1 is a schematic depicting one embodiment of the monitoring device of the present invention.

In one embodiment of the invention, there is provided a device configured to analyze blood, urine, or other fluid specimen in a nondestructive manner outside of a patient's arteries, veins, or other body compartment without removing the fluid specimen from a sterile environment. In particular, FIG. 1 is a schematic depicting one embodiment of the monitoring device 10 of the present invention. FIG. 1 shows a syringe acting as an access device 12 that is configured to receive a fluid specimen from a patient (not shown). The fluid specimen can be blood, urine, pus, or any other bodily fluid, such as those describe below. Device 10 has a fluid conduit 14 having therein a fluid channel. The fluid conduit can be (but is not limited to) fluid containers (e.g., syringe, bottles, tubes, etc.). The fluid conduit 14 is connectable to the access device 12 and is configured to hold the fluid specimen received from the patient. The fluid conduit 14 forms in one embodiment a sterile space contiguous with a body of the patient or a bodily fluid of the patient. Device 10 has an optical analyzer 16 configured to a) expose the fluid specimen in the fluid conduit 14 to incident light and b) measure a spectrum of light transmitted through the fluid conduit 14 and the fluid specimen.

In one embodiment of the invention, the optical analyzer 16 includes an optical housing 16a, a light source 16b, and a shutter 16c which directs light to the fluid channel on control. The shutter 16c can be configured to block the light path, as described above, to obtain the baseline spectral profile. The optical analyzer includes a spectrum analyzer 16d including an entrance lens 16e, a light dispersion element 16f (such as a grating or a prism), and detector 16g.

In addition to measuring a "dark current" for semiconductor detectors, a measurement with the shutter closed (in certain embodiments) or the illuminant source turned off (in other embodiments) can be used to compensate for ambient light that cannot be controlled. Light transmitted through the tubing and any fluid (e.g., saline, blood, urine) is received by detector 16g.

In one embodiment, also shown in FIG. 1, the device 10 may include an optical alignment rail 20, and one or more of the housings 16a and 16d may be located or relocated at desired distances from one another along the rail 20 by movement of either housing. The relative movement allows for opening the device to receive and secure a particular fluid conduit, and also allows the device to be used with a variety of alternative fluid conduits, other than just those which can be connected to a syringe or other access device 12. Other embodiments of the invention include ones that use rotating housings or other mechanisms for selective engagement with fluid conduits of varying sizes and mechanisms which place and locate a conduit in alignment with the path that light passes between the light source 16b and the detector 16g. In the cone embodiment, spectrum analyzer 16d includes a slit 16h. The sit 16h establishes the field of view for the detector 16d Spectrum analyzer 16d can be configured to measure light having a wavelength approximately between 360 nm (i.e., ultraviolet wavelengths) and 1100 nm (i.e., near-infrared wavelengths). Other embodiments may have a detector configured to detect light having other wavelengths, such as less than 360 nm or greater than 1100 nm. Furthermore, as shown, some embodiments can include optical lenses, or the like, such as lens 16e to direct and/or focus light onto the detector 16g. Still other embodiments may utilize narrow-band light emitters such as ultraviolet or near-ultraviolet LEDs to intentionally elicit fluorescence.

The optical analyzer 16 is not limited to any particular kind of light source or spectrum analyzer. As tested in this actual reduction to practice, a 2800K 5 W Halogen bulb was used as the light source. However, other lights sources such as light emitting diode LED (emitting at 365, 425 nm) could be used. In principle, laser light could be used for the light source. In this reduction to practice, an Avantes spectrometer was used which has approximately 1.5 nm resolution. It measured light intensity in the wavelength range 360-1100 nm. However, the invention is not limited and other more expansive or less expansive ranges can be used. In one embodiment, indicative of the mobile capability of the inventive device permitting it to be used at a patient's bedside, the light source 16b may be powered by a battery, however, other light sources and power supplies may be used, such as LEDs and AC connections, respectively.

Linearity of the spectral sensor is important because of the wide range in absorbance from saline and normal urine to blood and blood-tinged urine. The linearity of spectrometric devices from Avantes and Ocean Optics permits full-scale readings of attenuated spectra down to 0.001 (0.1%) or less. In one embodiment, the present invention uses the linearity of these spectrometers to implement autoexposure by increasing or decreasing the integration time to get readings that fill the dynamic range of the analogue to digital converter (ADC) in the spectrometer without clipping.

Figure 2A:
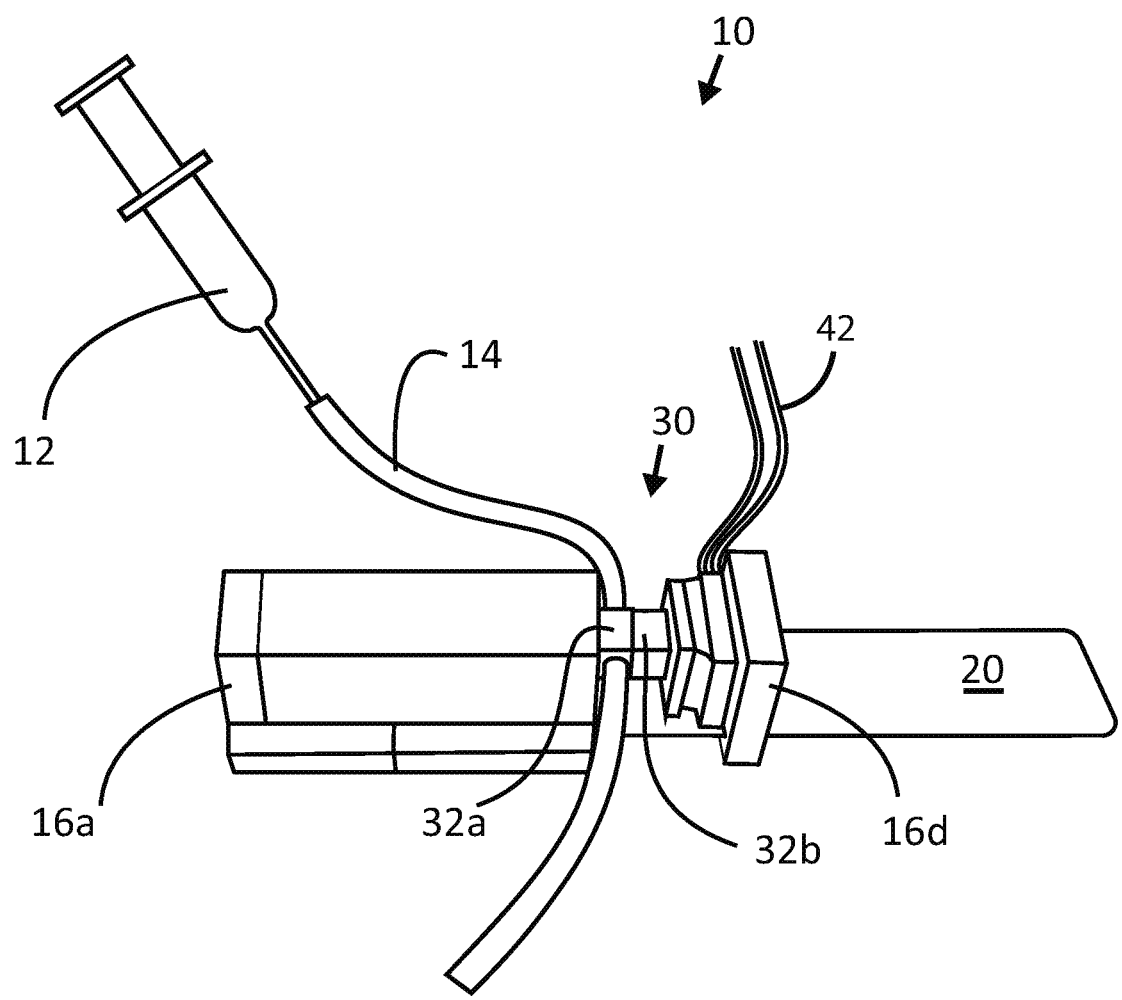
FIG. 2A is a depiction of the monitoring device according to one embodiment of the present invention including the optical rail and catheter mount.

In one embodiment of the invention, as shown in FIG. 2A, the monitoring device 10 includes an alignment rail 20 for ensuring alignment of the path of light exiting housing 16a and passing through a fluid sample (provided by a syringe 12 as an access device to a patient's body) in a fluid conduit 14, to be received by a detector 16g (not shown, see FIG. 1), connected to a processor/computer/control 40 by cable 42. The alignment rail 20 is in this embodiment a rigid rail which supports housing 16a and spectrum analyzer 16d, and which further supports a catheter, tubing, or other fluid conduit positioning device 30. Here, the catheter positioning device 30 includes a set of semi-circular jaws 32a and 32b that are configured to clamp the device 10 to the catheter. As used herein, "rigid" means that the alignment rail is strong enough to support the weight of the optical analyzer 16 and the conduit holder (e.g., jaws 32a and 32b) without deflection of the rail beyond a distance that would misalign the optical components mounted thereon. Other mechanical configurations may be employed, for instance hinges, provided that when the section with the light source and the section with the light collector (in some cases the spectrometer slit directly, in other cases various optical components such as lenses or mirrors directing light to spectrometer slit) are positioned around the fluid conduit, optical alignment is maintained at an acceptable tolerance over the range of conduit sizes the device can handle.

Figure 2B:
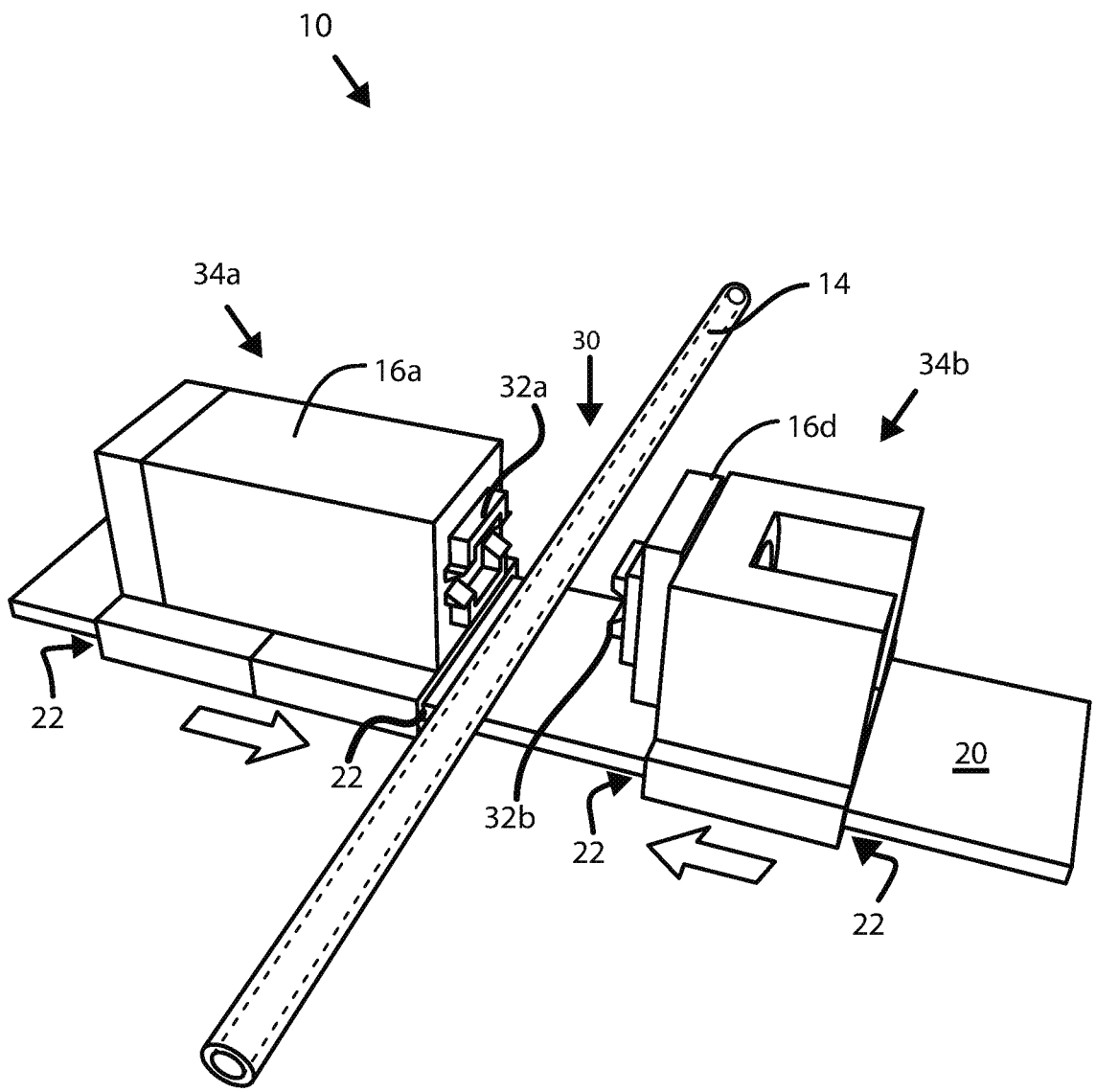
FIG. 2B is an expanded view showing the catheter coupling according to one embodiment of the monitoring device of the present invention.

In one embodiment of the invention, as shown in FIG. 2B, the catheter positioning device 30 includes a set of jaws 32a and 32b that are configured to clamp to catheter (or tubing) 14. In one embodiment, the jaws include a pair of blocks 34a, 34b slidably attached to rail 20 for opening and closing the jaws 32a, 32b. The blocks 34a, 34b and the rail 20 may have dovetail-type constructions 22 which permit precision location of one or blocks on the rail. In another embodiment, only one block opens and closes the jaws. In yet another embodiment, the jaws 32a, 32b include more than a pair of blocks. In still yet another embodiment, the jaws 32a and 32b open and close by rotating into place while being supported by rail 20. In the one embodiment, the jaws 32a, 32b conformally clamp to the catheter 14 without optically occluding the lumen of the catheter 14. In one embodiment, the jaws 32a and 32b, including the blocks 34a and 34b, have a semi-circular (e.g., concave-like) shape that fits to the tubing 14, which is typically circular in cross-section. The jaws 32a and 32b may be made of semi-rigid or moldable materials, such that the jaws can tightly form to the tubing 14.

Figure 2C:
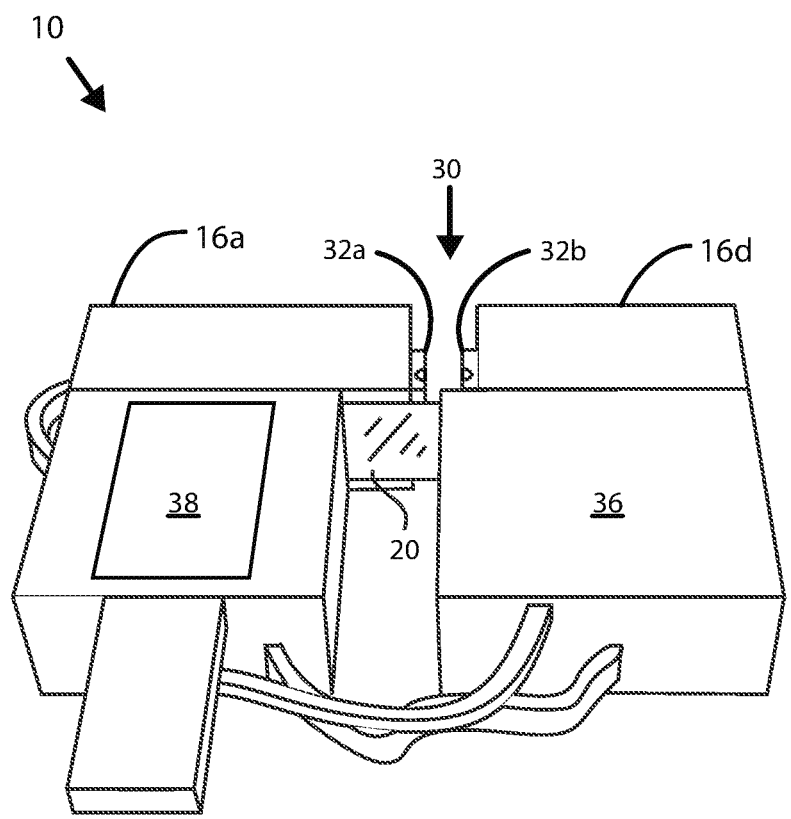
FIG. 2C is an overall view showing another embodiment of the monitoring device of the present invention.

FIG. 2C is a schematic depicting an overall view of the monitoring device 10 of the present invention. In this example, it comprises two housings. The housing on the left is an optical housing 16a which houses shutter 16c (not shown) in front of light source 16*b* (not shown); the housing on the right is a spectrum analyzer 16*d* which collects and focuses light that has travelled through a conduit between the two housings, into a spectrometer 36. The entire setup shown in FIG. 2C includes the two housings 16*a* and 16*d*, an alignment rail 20, the spectrometer 36, interface circuitry, a tungsten halogen bulb for the light source 16*b* (not shown), and a power source for the bulb (not shown). The device 10 is configured to attach to a controlling computer or controller via a USB cable (not shown).

Figure 2D:
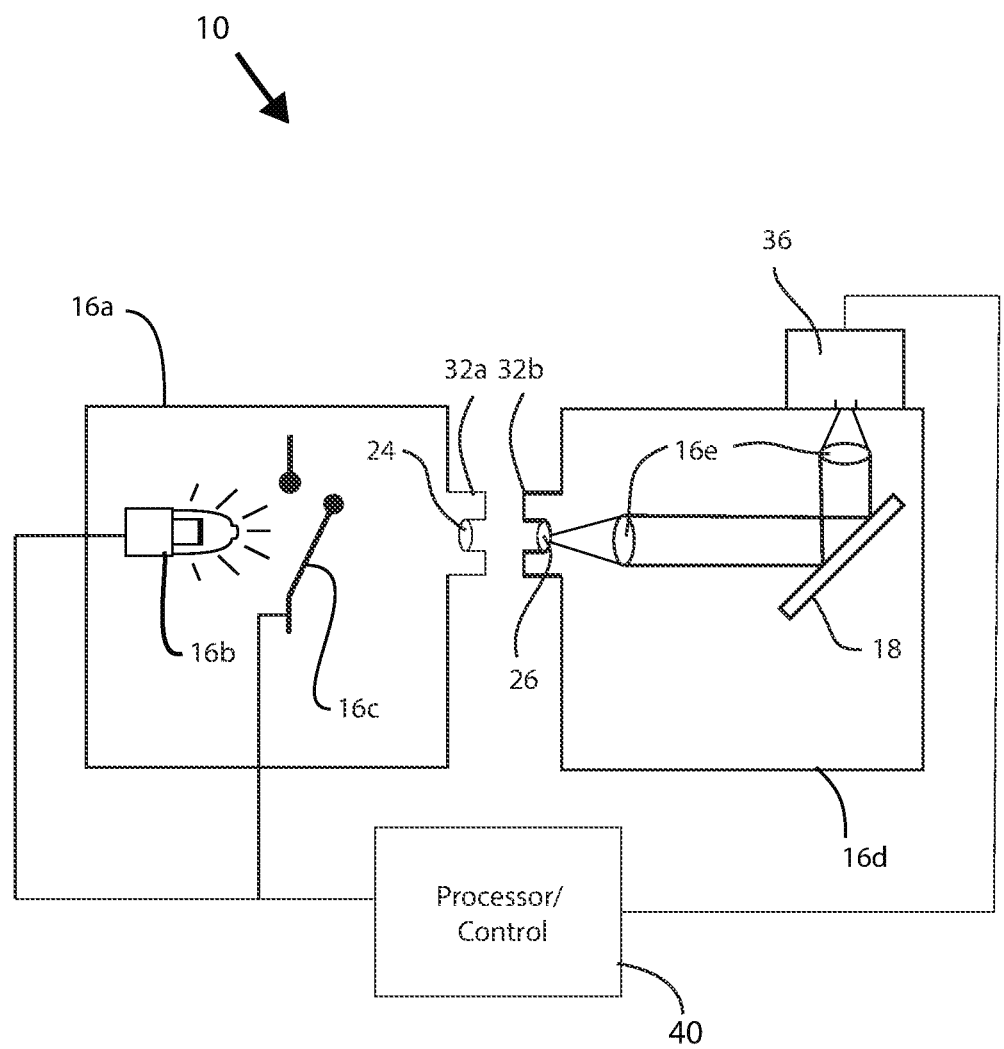
FIG. 2D is an overall view showing another embodiment of the monitoring device of the present invention.

FIG. 2D is a schematic depicting an overall view of the monitoring device 10 of the present invention, similar to that of FIGS. 1 and 2A-C. The optical housing 16*a* comprises a light source 16*b* and a shutter 16*c*. During operation of the device, the light source 16*b* may be left on, or may be turned on only when used to collect a spectrum. The shutter 16*c* shown is one that slides to open and close and is electromechanically controlled. However, other embodiments may be configured to use other shutters, such as ones which swing or radially open and close, or any other type of shutter. In the alternative, use of a different type of lighting (such as an LED or plural LEDs) that is adapted for momentary illumination may be used for light source 16*b* could allow for the shutter 16*c* to be omitted.

Housing 16*a* also comprises a sapphire window 24. The window 24 allows wavelengths of 200-5000 nm to exit the housing 16*a*, such that light within that range of wavelengths exit the semi-circular jaw 32*a* and are passed into and through a tube, vial, or other fluid conduit containing a fluid sample (not shown). Housing 16*d* comprises a semi-circular jaw 32*b*, which locates the fluid conduit (not shown) in alignment with the jaw 32*a*, such that light exiting the fluid conduit (not shown) reaches a window diffuser 26 on the housing 16*d*. In one embodiment, window 26 permits mainly light from 350-2000 nm wavelengths (a narrower range than the sapphire window 24) to enter the receiving housing/spectrum analyzer 16*d*. Here, in this embodiment, the light which passes the window 26 passes through a lens 16*e*, and is redirected with a mirror 18, before passing through another lens 16*e*, to be received by a spectrometer 36.

The spectrometer 36, light shutter 16*c*, and light source 16*a* are all controlled by a control system comprising a processor and control circuitry 40. The processor and control circuitry 40 have inputs and outputs with respect to the spectrometer 36, shutter 16*c*, and light source 16*a*, and to receive inputs-from and report outputs-to either a directly connected or wirelessly connected interface device or system, such as wireless communications or a USB cable or other physical connection with a tablet or computer configured to input and output with the control system (not shown).

In one embodiment of the invention, device 10 is a portable device about the size of a modern smartphone, or any other words, device 10 is a hand-held device which, in one embodiment. has a fluid conduit 14 holding a fluid specimen received from the patient in a sterile space contiguous with a body of the patient for measurement by an optical analyzer 16 of the optical properties of the fluid specimen.

In other embodiments of the invention, the fluid conduit 14 may comprise a tube, the optical alignment mechanism (e.g., rail 20) may further comprise a tube alignment channel and tube retainer which secures the tube. Further, the catheter positioning device 30 may comprise any of the following types in-place-of or in-addition-to jaws, such as jaws 32*a* and 32*b*: tube clips, tube ties, tube clamps, tube channel tabs, tube holders, tube channel retaining tabs and tube retaining geometry. The channel may have at least one point along the length of its cross section which deviates from a predominant lengthwise axis. For example, compression of the fluid conduit 14 to provide friction that retains the conduit in place may reduce (flatten) the fluid conduit 14 at one place along the length of the fluid conduit 14.

Figure 3:
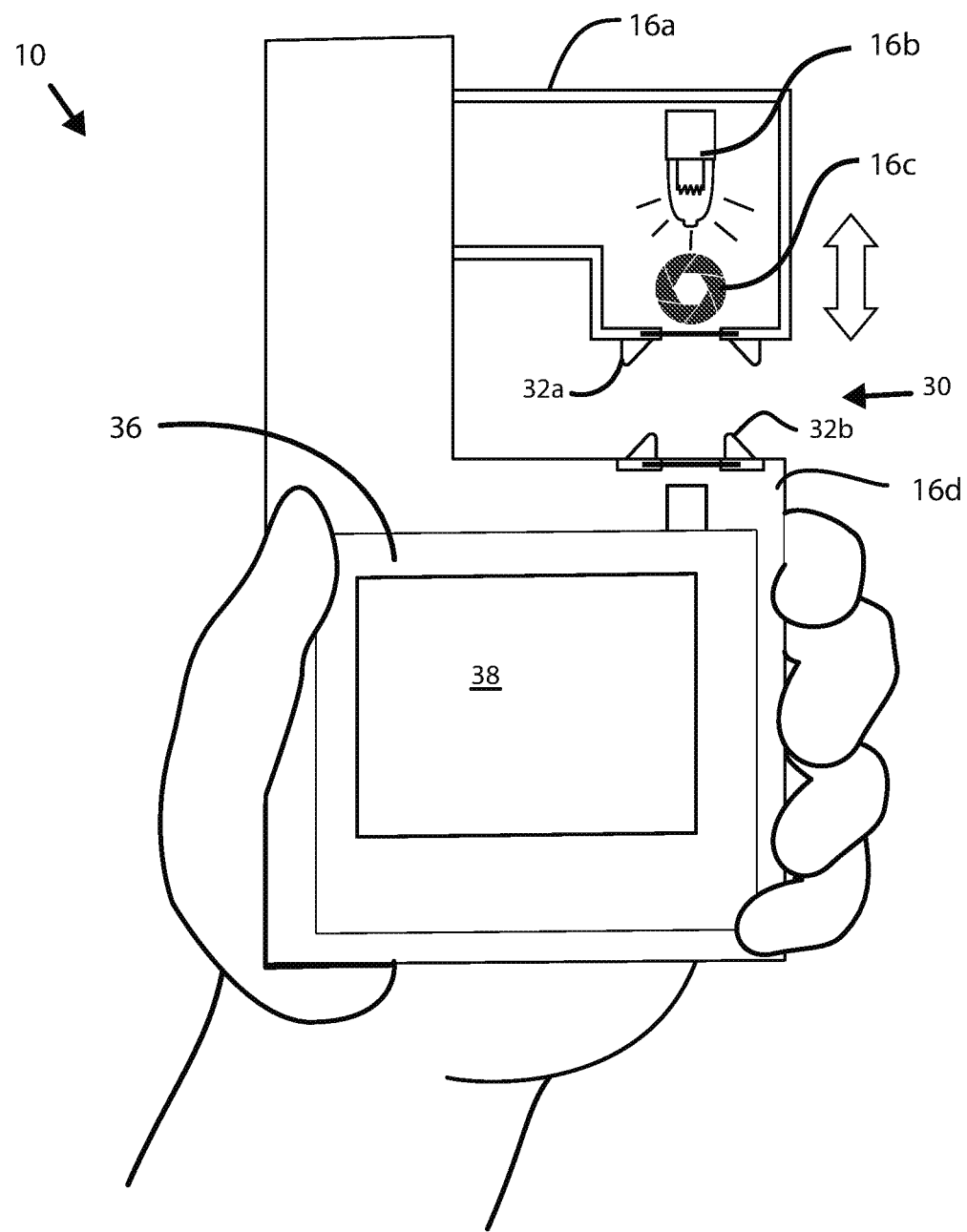
FIG. 3 is a schematic depicting the monitoring device according to another embodiment of the present invention.

FIG. 3 is a schematic another monitoring device 10 of the present invention illustrating in this embodiment the mobility or portability of the monitoring device such that it can be used at a patient's side. Like FIGS. 1 and 2A-C, there is shown an optical housing 16*a* and a spectrum analyzer housing 16*d*. The optical housing 16*a* comprises a light source 16*b* and a shutter 16*c*, and a jaw 32*a*. The spectrum analyzer housing 16*d* comprises a jaw 32*b* and a spectrometer 36, such as an Avantes spectrometer, having an LCD display 38. The device is shown in a handheld embodiment with the spectrum analyzer housing 16*d* being held in one hand of a user, and with a clear view of the LCD display 38, unobstructed by the hand holding the device 10.

In this configuration, as shown, the optical housing 16*a* can translate vertically toward 16*d*, such that a permit fluid conduit 14 (not shown) can be placed between the jaws 32*a* and 32*b*, to securely locate the fluid conduit. The jaws 32*a*, 32*b* shown are of an overlapping and intersecting wedge-type, but other contemplated embodiments are configured to grasp fluid conduits and other fluid containing vessels with other shapes, such as semi-circular jaw shapes configured to secure tubing-types of fluid conduits, such as a catheter. In this position, a fluid conduit can be secured in alignment with light exiting the optical housing 16*a*, such that light may pass into the fluid conduit and through a fluid sample (not shown) within the lumen of the conduit and enter the housing 16*d*. The light which enters the spectrum analyzer housing 16*d* then enters the spectrometer 36, for analysis.

The analysis carried out using the spectrometer 36 is able to be controlled and monitored by a user viewing the LCD display 38. Alternatively, the LCD display 38 may be configured to control other components of the device 10, such as the positioning of the housing 16*a*, the operation and timing of the light source 16*b* and shutter 16*c*, in addition to conducting the analysis and any steps thereof, as well as displaying results or other relevant information about the device 10 and data of an instance of an analysis performed or in process by the device 10.

In one embodiment, the device 10 is configured to couple to a fluid conduit 14 comprising tubing attached to indwelling arterial or venous catheters. Outside of a patient, device 10 permits one to take and assess data from within the vasculature or other areas within the body (e.g., cerebral ventricles). More than just blood can be sampled. More specifically, device 10 can assess properties of various body fluids e.g., cerebrospinal fluid, urine, peritoneal fluid, or pleural fluid (see FIG. 9). Furthermore, the sterile environment of the fluid conduit 14 permits one to assess serial assessments of an existing Foley catheter or intracavity tube. For example, for urinary catheters, saline-filled tubing can be replaced with air-filled tubing; blood-filled tubing can be replaced with urine-filled tubing. The specimen should ideally not be moved along the conduit 14 while the device 10 is performing measurements. Plastic clamps found on the fluid conduits 14 comprising Foley catheter tubing can be used to block urine above the optical analyzer 16 for the air reading, and then be used block urine flow below the measurement site of the analyzer 16, such that the fluid conduit 14 is filled with urine for the sample reading (after the air reading).

Catheters provide one type of port to fluids of a patient's body. In several uses, a catheter is used to remove blood from the patient for lab testing at a location that is remote to the location of the patient. In one embodiment of this invention, blood is kept in a sterile space in a fluid conduit 14 that is contiguous with the patient's bloodstream. For example, a fluid conduit 14 may comprise a catheter comprising tubing, and the device 10 can be specifically configured to optically analyze the blood in the tubing. After analysis, the blood can be flushed back into the patient's vascular space with minimal disruption. Thus, device 10 can provide blood oxygenation and other measurements even in pulseless or low-flow states to provide useful patient-relevant information while minimizing effects to physiologic homeostasis.

When no indwelling vascular catheter exists in a patient, such as in an outpatient clinic setting, blood needed for testing is removed from the patient, temporarily stored in an access device 12, such as a syringe, and injected into a more secure storage vial. In this embodiment, device 10 can also be utilized to obtain the spectroscopic signal of the blood or other bodily fluids, thus preventing the need for blood transport and therefore reducing the delay to acquire relevant clinical information.

In this embodiment, the fluid conduit 14 need not be in a space contiguous with a body of the patient or a bodily fluid of the patient, although access device 12 could be attached to a needle in the patient, to draw blood, and then be delivered directly from the access device 12 into the optical analyzer 16. Moreover, the fluid itself drawn and the fluid conduit 14 may or may not be sterile. For example, in a sterile state, device 10 could assess the presence of fungal wall fragment in blood. In a sterile state, sterile cerebrospinal fluid inside a sterile catheter residing in the ventricles of the brain (i.e., intraventricular drain) can be analyzed In an unsterile state, device 10 could assess the pleural total protein level in a chest tube drainage container.

In one embodiment, where blood is routinely drawn into vials and removed from the patient, the optical analyzer 16 is configured to accommodate the vials for optical analysis. In this embodiment, calibration vials filled with air are provided for a baseline optical measurement, prior to measuring the vials.

Figure 4A:
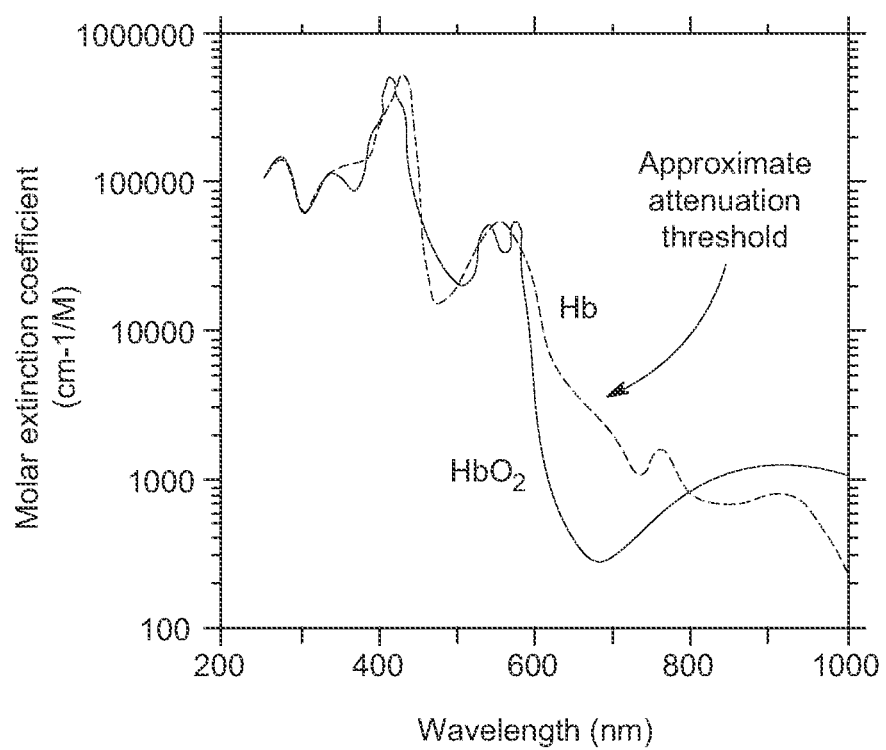
FIG. 4A is a graph of an optical transmission spectrum through a catheter contain blood from a patient.
Figure 4B:
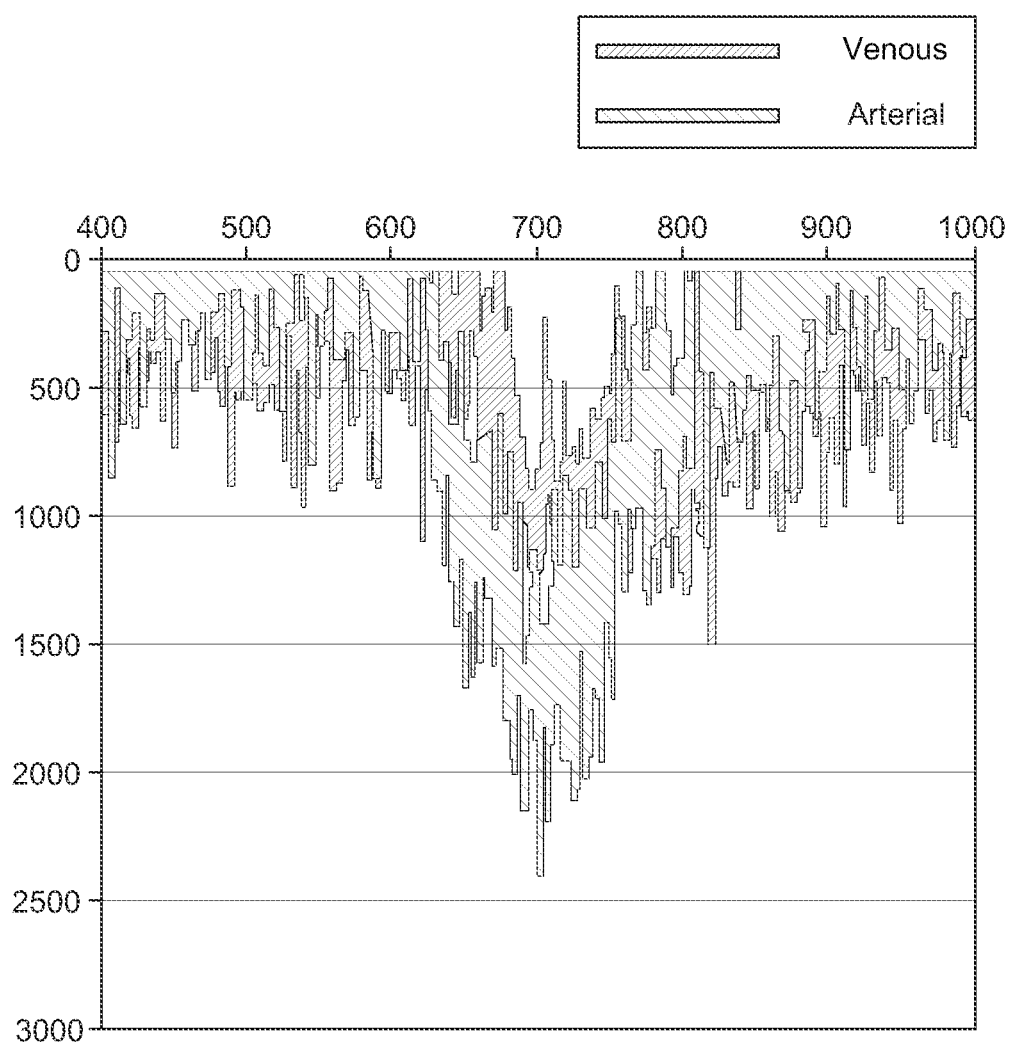
FIG. 4B is another graph of an optical transmission spectrum through a catheter contain blood from a patient.

In other embodiments, various preapproved/prefilled tubes or vials (e.g., CBC or blood culture tubes) can be used for calibration purposes or baseline adjusting. Once validated, measurements and analysis can focus on the comprehensive description of blood or other bodily fluid using for example a high-resolution spectrometer. Spectral waveforms such as shown in FIGS. 4A and 4B can be captured in aggregate data (for example as a sum or product of a number of large- and small-signal components). The data can thereafter be stored in controller 40.

Hence, device 10 can analyze and store data for a wide variety of specimens (e.g., venous or arterial blood, urine, CSF, pleural fluid, peritoneal fluid) for anything (e.g., ultimately bacteria, cellular DNA fragments, proteins, electrolytes) in/on the body. Some examples are intravascular blood contents, extracorporeal blood contents (e.g., blood circulating within ECMO or CRRT circuit), cerebral ventricles (e.g., inside brain itself or in intraventricular drain tubing lying external to the patient), pleural space, pericardial space, intravascular coronary artery composition, bladder wall tumor, skin and others.

In one embodiment of the invention, the device 10 is configured to capture a high-resolution spectral transmittance profile over a broad wavelength range that is a superset of the information obtained with existing devices. During clinical testing, the device 10 can be configured to replicate existing medical tests (e.g., oxygen saturation of hemoglobin). Replicating existing tests would demonstrate that the device is obtaining accurate, medically-relevant information about a patient's condition.

In one embodiment of the invention, the device is configured to transform biologic specimens (taken from a patient) into corresponding comprehensive numeric descriptive information at the patient's bedside. Rather than transporting biologic specimens to the lab for analysis, device 10 can either transmit the numeric information to a server for analysis using any capable (i.e., existing or future) communication technique or process the information internally within the device 10. This intervention can substantially reduce the need for consumable labware and specialized specimen containers, simplifying transport logistics, while minimizing the risk of accidental disease transmission or human error. In another embodiment of the invention, the device 10 can be configured with artificial intelligence algorithms and machine-learning methods (e.g., supervised learning systems as well as unsupervised learning, on either the device 10, computer/processor/circuitry 40, or a server in wireless communication with the device 10).

Accordingly, device 10 can be configured to analyze biologic specimens in a nondestructive manner either inside (e.g., arterial or venous vasculature, body cavity) or outside (e.g., vascular tubing, specimen container) of a patient's body. Device 10 can be configured to couple to a hollow object such as tubing attached to indwelling arterial or venous catheters. These catheters are often the ports through which blood is removed from the patient for lab testing. Blood in such tubing is in a sterile space contiguous with the patient's bloodstream. The device can be further configured to optically analyze the blood in the tubing, just as it could analyze urine within the lumen of tubing attached to indwelling urinary catheters. After analysis, the blood can be flushed back into the patient's vascular space with minimal disruption. Device 10 can thereby provide blood oxygenation and other measurements even in in pulseless or low-flow states.

In one embodiment of the present invention, device 10 can be further configured to measure in situ many clinically-relevant parameters which typically require a tube of blood to be removed from the patient for testing. For example, device 10 can be a small gun-like handheld device that can accommodate tubing of any size or made of any translucent substance (e.g., IV tubing, blood tube containers used for outpatient blood draws, thoracostomy catheter tubing, or Foley catheter tubing). As such, device 10 can be used in any environment (e.g., battlefield, resource-limited setting, major medical center, outpatient clinic). Thus, the device 10 can provide quantitative assessments of blood contents faster than typical methods, such as within seconds, at many patients' bedsides instead of having to wait for extended periods of time (e.g., hours to days) for laboratory results.

Figure 8:
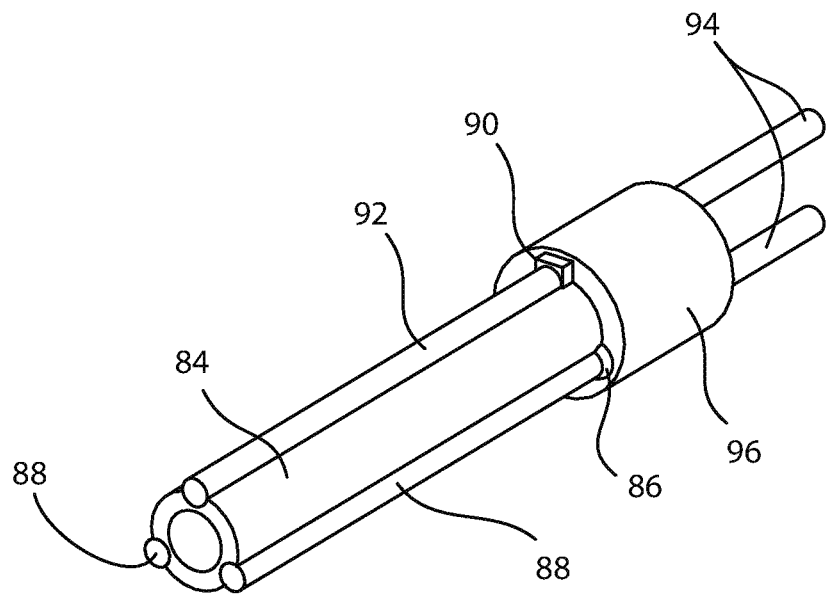
FIG. 8 is an overall view showing another embodiment of the monitoring device, such as for intravascular use, of the present invention.
Figure 8:
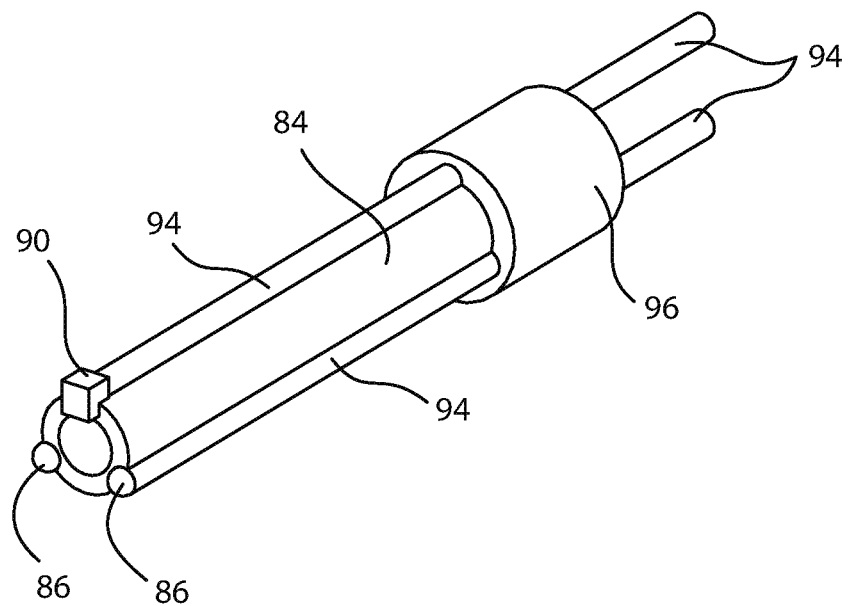

In one embodiment of the invention, light transmitters/detectors could be integrated into intravenous, intraarterial, or any intracavitary tubing of a fluid conduit, so as to allow real-time, in vivo fluid content analyses (e.g., instead of a normal arterial catheter being inserted, a clinician would insert an arterial catheter with our light transmitters/detectors integrated into the catheter). Referring to FIG. 8, an overall view of this configuration for intravascular use is shown. As depicted, a tube 84 (fluid conduit) has disposed thereon light emitting diodes (LEDs) 86 and a fiber optic 88 which disperses light through the wall of tube 84 into the fluid contained therein. While the invention is not so limited, in the embodiment depicted, there are two LEDs arranged at different angular positions and propagating light into corresponding fiber optics 88. Light transmitted through the fluid is collected by a photodiode 90 which may be receiving light directly from the tube 84 or light received along another fiber optic 92 extending along a length of tube 84. As shown in FIG. 8, wires 94 for powering the LEDs 86 or collecting signals from the photodiode 90 can routed through a hub 96.

In one embodiment, the fiber optics may not be used. Instead, tube 84 has a plurality of LEDs 86 and a plurality of photodiodes 90 disposed in opposition along a longitudinal length of tube 84. In one embodiment, the plurality of LEDs 86 may have different emission wavelengths and be operated sequentially such that different absorptions for different compounds (or the same compound) in the optical path can be measured.

In one embodiment of the present invention, the device 10 is configured to be portable and handheld, and optionally can couple to walls of tubing of a fluid conduit 14 that is attached to intravascular cannulas. In one embodiment, the device couples to the wall of such tubing. The central space (lumen) of the tubing can be flushed (e.g., filled) with sterile water, saline, or other innocuous substance to displace any bound or other preexisting fluid contents. A syringe or other access device 12 can also draw blood back from the intravascular space into the tubing. The device 10 provides broadband illumination that covers the spectral region of interest. This light travels through the walls of the tubing and the contents of the tubing (~specimen in the fluid conduit 14), resulting in absorption and other interactions with the matter it encounters as it passes through the fluid conduit 14. The device 10 is further configured to block light from the light source 16b to obtain the sum of "dark current" (a nonzero contributor to the total photon counts detected by semiconductor photodetectors that occurs even in the absence of illumination) and ambient light leakage.

In one embodiment of the present invention, the device 10 is configured to analyze a specimen of blood in a fluid conduit 14 by obtaining three spectral profiles of light transmitted through approximately transparent tubing of the conduit 14: a reference spectral profile of the illuminating light through tubing filled with sterile saline or water; an ambient (traditionally "dark") spectral profile; and the spectral profile of the illuminating light through blood drawn back into the tubing. The spectral profile of the illuminated saline-filled tube, less the spectral profile obtained with the light source 16b blocked, represents the maximum possible light at each wavelength that can be absorbed by constituents of the sample.

The spectral profile of light travelling through the blood (or other biological specimen) drawn back into the tubing, less the dark/ambient contribution divided by the maximum absorbable light determined above, yields a fractional absorption at each wavelength (assuming there is no spontaneous or excited emission, such as phosphorescence or fluorescence). This absorption profile reflects the aggregate absorptivity of innumerable components of blood (or other biologic specimen). Other embodiments could use narrowband short-wavelength light, such as that emitted by ultraviolet or near-ultraviolet light emitting diodes, to intentionally elicit autofluorescence as yet another independent set of measurements characterizing the complex aggregate within the tubing of the fluid conduit 14.

For example, in one embodiment of the invention, the optical analyzer 16 could use for the light source a 365 nm UV LED emitter, in which case (auto) fluorescence spectral measurements could be made, examining fluorescence of the sample from 400-1000 nm using essentially the same method and setup as shown in FIG. 1. However, instead of obtaining a dark/ambient reading and then a halogen-illuminated reading of the saline-filled tube, and followed by the blood-filled tube, the device would obtain a dark/ambient reading, a halogen+blue illumination reading, and a UV-only illuminated reading of the saline-filled tube, before repeating with blood-filled tube.

After subtracting the dark/ambient counts from the other readings, the controller 40 would be programmed to divide the numbers in the blood-illuminated-by-halogen+blue vector by the numbers in the saline-illuminated-by-halogen+blue vector to get transmittance (1-absorbance) information/data. The controller 40 would then be programmed to subtract the numbers in the saline-illuminated-by-UV vector from the numbers in the blood-illuminated-by-UV vector, to estimate the autofluorescence (from blood components).

In one embodiment of the present invention, tubing of a fluid conduit 14 is coupled to the indwelling catheter and acts as a "living cuvette." The tubing receives blood, such as by using an access device 12 (such as a syringe), as though the blood was going to be placed into specimen tubes for transport to the laboratory, and the device obtains the full spectral profile (e.g., spectral profile of the blood in the tubing that is illuminated by the light source). The blood drawn back into the tubing can be flushed back into the vascular space, resulting in negligible blood loss. Thus, unlike traditional lab draws and point-of-care testing, the patient's blood remains in a sterile intravascular and intraluminal continuum. Also, device 10 can be configured to avoid direct contact with the blood and be cleaned and/or remain sterile between patients.

As a further advantage, the device 10 can obtain the blood spectral profile faster than typical measurements, because device 10 is configured to analyze the spectral profiles without requiring testing at a location that is remote to the location of the patient, with each spectral sample able to be obtained on the order of fractions of a second. Further, device 10 is congruent with typical safety protocols for handling blood. For example, drawing blood into the tubing and flushing the tubing with sterile saline is standard operating procedure for any arterial or venous blood draw from an indwelling vascular catheter. Thus, device 10 and the method of use thereof does not substantially increase the operator time, or reduce safety, with the patient compared to typical devices and methods.

In one embodiment of the invention, the device 10 is configured to analyze a biologic specimen without removal of the specimen from the patient and transportation to a lab. The analysis can be transmitted by a control system, processor, computer, or control circuitry 40 as a signal through a wired or wireless communication link, such as Wi-Fi, cellular, satellite radio, or the like, to external physicians, medical staff, or storage. This is valuable for several advantages, such as to reduce handling of biohazardous material by medical staff and significantly more efficient processing time.

In one embodiment of the invention, device 10 could include software that is configured to determine a composite attenuation waveform (e.g., using the spectral profiles discussed above). The device 10 further could analyze the composite attenuation waveform as an aggregate of signals of varying amplitude, to measure clinical values. The device 10 is further configured to analyze the composite attenuation waveform when the length of the light path (e.g., from the light source to the detector) through a fluid conduit 14 is unknown. For example, analyzing the composite attenuation waveform may include estimating a mean path length through the blood sample that is independent of dimensions of the tubing by averaging attenuation of known analytes at different wavelengths.

Referring now to FIGS. 4A and 4B, what is shown are raw attenuation patterns of hemoglobin and oxyhemoglobin in arterial and venous samples from a canine subject. The relative differences between oxyhemoglobin (arterial, 100% oxygen saturation as confirmed by point-of-care blood gas analysis and pulse oximetry) and the venous mix of equal parts hemoglobin and oxyhemoglobin are apparent. Also, direct correlation with the in vitro spectral absorbance properties of hemoglobin and oxyhemoglobin can be noted.

As to FIG. 4B, what is shown pertains to an uncorrected transmission pattern using an embodiment of the invention comprising a light source comprising a tungsten-halogen lamp. Note that the sensitivity of the spectrometer used can be very low for wavelengths that are greater than 900 nm.

Computerized Control of Monitoring Device

Figure 5:
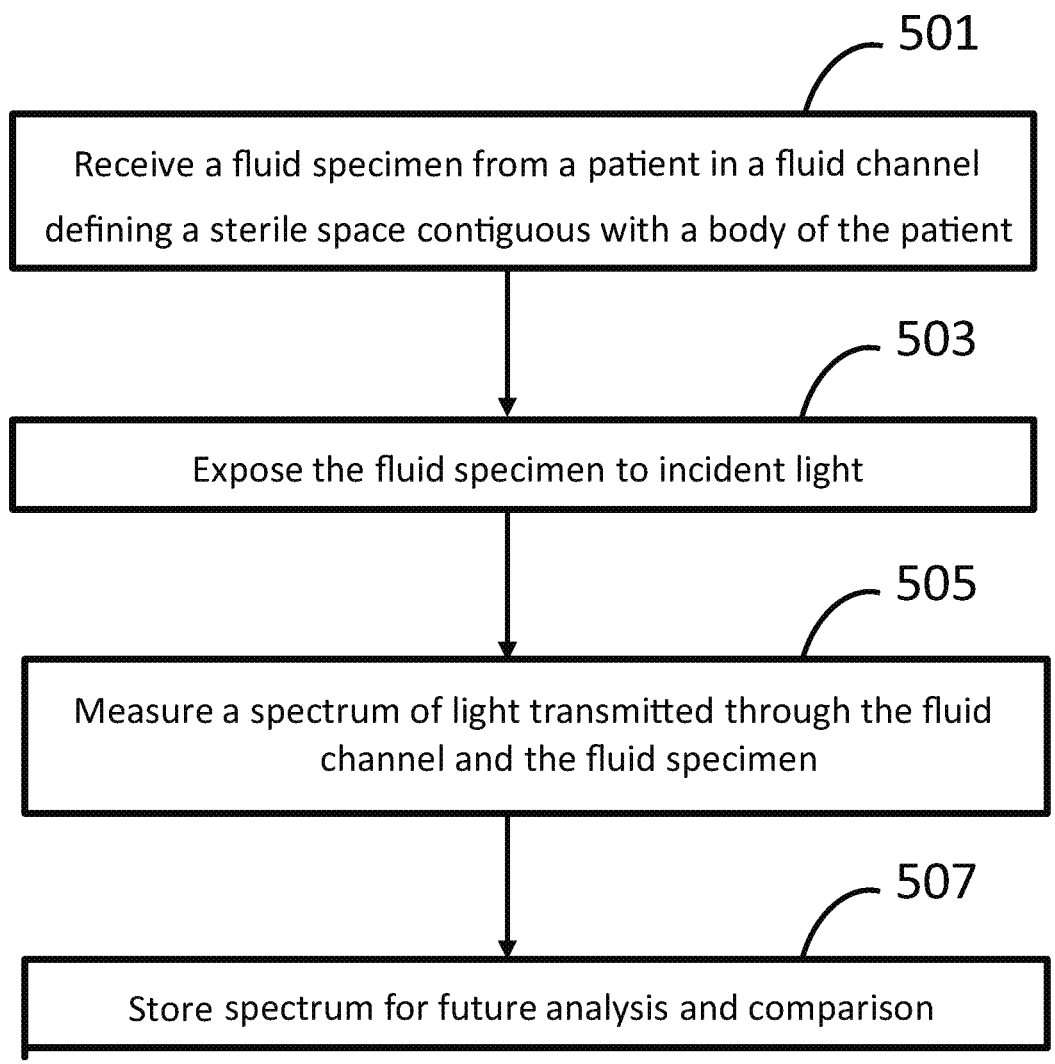
FIG. 5 is a flow chart depicting one method of the present invention for using the devices described above.

In accordance with embodiments, the invention is configurable for implementation with a computer. FIG. 5 is a flow chart depicting one method of the present invention for using the monitoring devices described above. Referring now to FIG. 5, what is shown is a series of steps for carrying out a method for monitoring at least one parameter of a fluid specimen obtained from a patient using the device noted above.

In this method, at 501, a fluid specimen is received from a patient in a fluid channel defining a sterile space contiguous with a body of the patient. At 503, the fluid specimen in the fluid channel is exposed to incident light. At 505, a spectrum of light transmitted through the fluid channel and the fluid specimen is measured. At 507, the spectrum is stored for further analysis and comparison.

Figure 6:
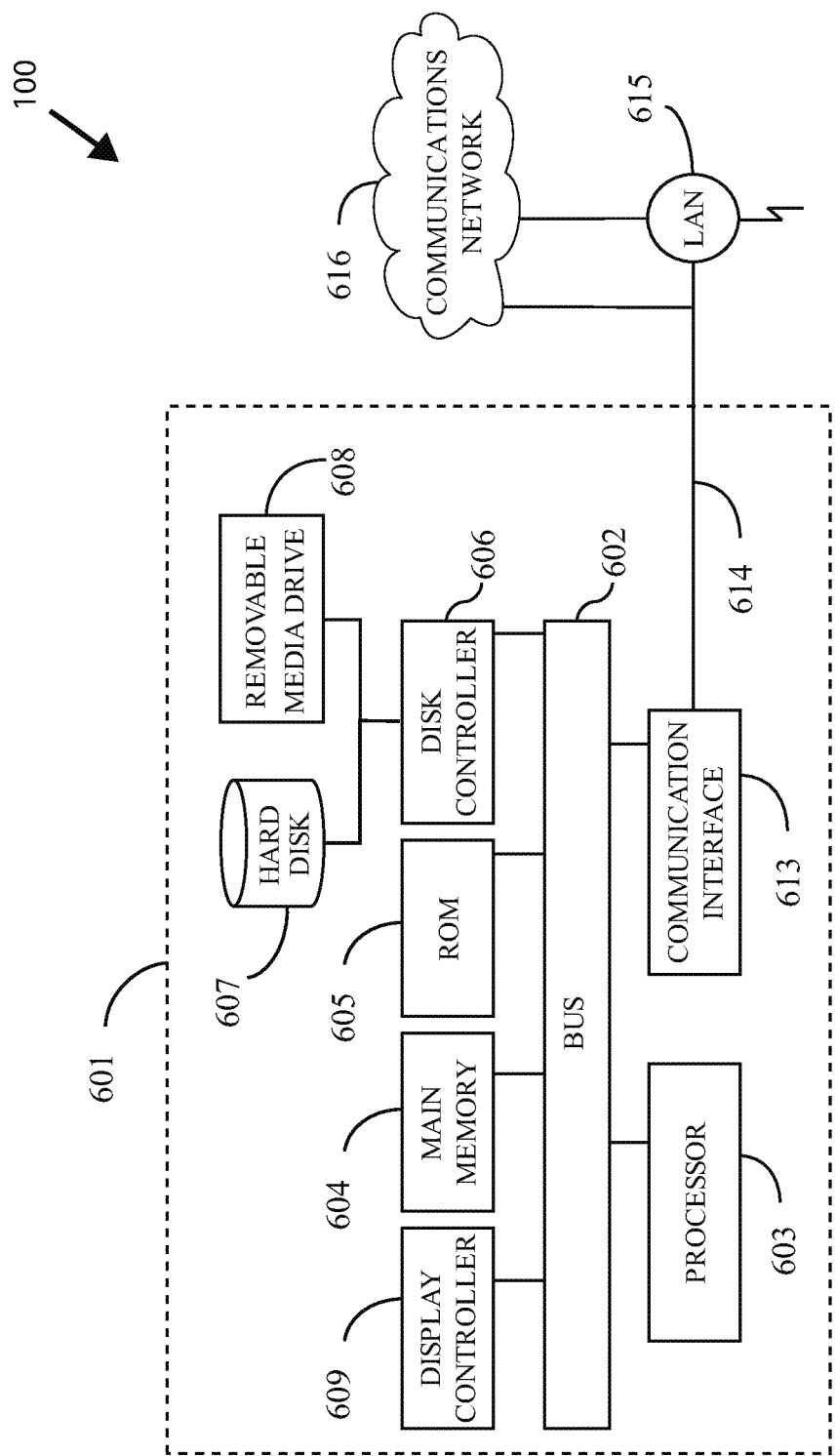
FIG. 6 is a computer system 601 for implementing various embodiments of the invention.

FIG. 6 illustrates a computer system 601 for implementing various embodiments of the invention. In particular, computer system 601 may be used as control system 100 to perform any or all of the functions described above, including some or all of the steps described in FIG. 5 (and any of the controlled steps set forth in FIG. 7 below). The computer system 601 includes a bus 602 or other communication mechanism for communicating information, and a processor 603 coupled with the bus 602 for processing the information. The computer system 601 also includes a main memory 604, such as a random access memory (RAM) or other dynamic storage device (e.g., dynamic RAM (DRAM), static RAM (SRAM), and synchronous DRAM (SDRAM)), coupled to the bus 602 for storing information and instructions to be executed by processor 603. In addition, the main memory 604 may be used for storing temporary variables or other intermediate information during the execution of instructions by the processor 603. The computer system 601 further includes a read only memory (ROM) 605 or other static storage device (e.g., programmable read only memory (PROM), erasable PROM (EPROM), and electrically erasable PROM (EEPROM)) coupled to the bus 602 for storing static information and instructions for the processor 603.

The computer system 601 also includes a disk controller 606 coupled to the bus 602 to control one or more storage devices for storing information and instructions, such as a magnetic hard disk 607, and a removable media drive 608 (e.g., floppy disk drive, read-only compact disc drive, read/write compact disc drive, compact disc jukebox, tape drive, and removable magneto-optical drive). The storage devices may be added to the computer system 601 using an appropriate device interface (e.g., small computer system interface (SCSI), integrated device electronics (IDE), enhanced-IDE (E-IDE), direct memory access (DMA), or ultra-DMA).

The computer system 601 may also include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

The computer system 601 may also include a display controller 609 (such as the display 38 in FIG. 3) coupled to the bus 602 to control a display, such as a cathode ray tube (CRT), for displaying information to a computer user. The computer system includes input devices, such as a keyboard and a pointing device, for interacting with a computer user and providing information to the processor 603. The pointing device, for example, may be a mouse, a trackball, or a pointing stick for communicating direction information and command selections to the processor 603 and for controlling cursor movement on the display to a user.

The computer system 601 performs a portion or all of the processing steps of the invention (such as for example those described in relation to FIG. 5 or FIG. 7) in response to the processor 603 executing one or more sequences of one or more instructions contained in a memory, such as the main memory 604. Such instructions may be read into the main memory 604 from another computer readable medium, such as a hard disk 607 or a removable media drive 608. One or more processors in a multi-processing arrangement may also be employed to execute the sequences of instructions contained in main memory 604. In alternative embodiments, hard-wired circuitry may be used in place of or in combination with software instructions. Thus, embodiments are not limited to any specific combination of hardware circuitry and software.

As stated above, the computer system 601 includes at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Stored on any one or on a combination of computer readable media, the invention includes software for controlling the computer system 601, for driving a device or devices for implementing the invention, and for enabling the computer system 601 to interact with a human user. Such software may include, but is not limited to, device drivers, operating systems, development tools, and applications software. Such computer readable media further includes the computer program product of the invention for performing all or a portion (if processing is distributed) of the processing performed in implementing the invention.

The computer code devices of the invention may be any interpretable or executable code mechanism, including but not limited to scripts, interpretable programs, dynamic link libraries (DLLs), Java classes, and complete executable programs. Moreover, parts of the processing of the invention may be distributed for better performance, reliability, and/or cost.

The term "computer readable medium" as used herein refers to any medium that participates in providing instructions to the processor 603 for execution. A computer readable medium may take many forms, including but not limited to, non-volatile media, volatile media, and transmission media. Non-volatile media includes, for example, optical, magnetic disks, and magneto-optical disks, such as the hard disk 607 or the removable media drive 608. Volatile media includes dynamic memory, such as the main memory 604. Transmission media includes coaxial cables, copper wire and fiber optics, including the wires that make up the bus 602. Transmission media also may also take the form of acoustic or light waves, such as those generated during radio wave and infrared data communications.

Various forms of computer readable media may be involved in carrying out one or more sequences of one or more instructions to processor 603 for execution. For example, the instructions may initially be carried on a magnetic disk of a remote computer. The remote computer can load the instructions for implementing all or a portion of the invention remotely into a dynamic memory and send the instructions. The bus 602 carries the data to the main memory 604, from which the processor 603 retrieves and executes the instructions. The instructions received by the main memory 604 may optionally be stored on storage device 607 or 608 either before or after execution by processor 603.

The computer system 601 also includes a communication interface 613 coupled to the bus 602. The communication interface 613 provides a two-way data communication coupling to a network link 614 that is connected to, for example, a local area network (LAN) 615, or to another communications network 616 such as the Internet. For example, the communication interface 613 may be a network interface card to attach to any packet switched LAN. As another example, the communication interface 613 may be an asymmetrical digital subscriber line (ADSL) card, an integrated services digital network (ISDN) card or a modem to provide a data communication connection to a corresponding type of communications line. Wireless links may also be implemented. In any such implementation, the communication interface 613 sends and receives electrical, electromagnetic or optical signals that carry digital data streams representing various types of information.

The network link 614 typically provides data communication through one or more networks to other data devices. For example, the network link 614 may provide a connection to another computer through a local network 615 (e.g., a LAN) or through equipment operated by a service provider, which provides communication services through a communications network 616. The local network 614 and the communications network 616 use, for example, electrical, electromagnetic, or optical signals that carry digital data streams, and the associated physical layer (e.g., CAT 5 cable, coaxial cable, optical fiber, etc). The signals through the various networks and the signals on the network link 614 and through the communication interface 613, which carry the digital data to and from the computer system 601 may be implemented in baseband signals, or carrier wave-based signals. The baseband signals convey the digital data as unmodulated electrical pulses that are descriptive of a stream of digital data bits, where the term "bits" is to be construed broadly to mean symbol, where each symbol conveys at least one or more information bits. The digital data may also be used to modulate a carrier wave, such as with amplitude, phase and/or frequency shift keyed signals that are propagated over a conductive media, or transmitted as electromagnetic waves through a propagation medium. Thus, the digital data may be sent as unmodulated baseband data through a "wired" communication channel and/or sent within a predetermined frequency band, different than baseband, by modulating a carrier wave. The computer system 601 can transmit and receive data, including program code, through the network(s) 615 and 616, the network link 614, and the communication interface 613. Accordingly, as described above, device 10 can either transmit numeric information to a server for analysis or process the information internally within the device 10.

Implementation and Use of Monitoring Device

In accordance with various embodiments of the invention, one embodiment is a method of performing measurements for monitoring at least one parameter of a fluid specimen obtained from a patient. Patients as used herein refer to principally to human and animal patients. However, it is noted that this invention has utility for use in any environment where there is a need to analyze a fluid spectrum by spectroscopy on site. Some examples include bacterial testing of water at a sewage treatment facility to determine changes in content, medication monitoring of patients' urine or blood to assess medication adherence, screening of patients' bodily fluids to both determine the presence of and to quantify chemical content (e.g., cocaine, botulism toxin, synthetic cannabinoid, anthrax). For example, this invention can be used for routine drug screening, rapid screening for bioterrorism-based toxins, checking lead levels in children in at-risk housing, running a body fluid screen of any toxicologic substance in a sick obtunded patient unable to provide a medical history (or a dead body at the medical examiner's office). Other uses include screening blood for the presence of circulating malignant cells as a means of early cancer detection, assessing hormonal deficiencies at the bedside to help deliver personalized medical therapy rapidly for less cost, assessing the purity and contents of various types of beer, wine or other spirits, for use when going camping to ensure water purity in mountain streams or for use in a resource-limited country to identify risks of acquiring a diarrheal illness. A person at a bar could use the inventive device to check for substance in his/her drink such as a roofie. People could use the inventive device to analyze sputum samples in order to rapidly diagnose tuberculosis in international travelers at airports entering a country.

The catheter with the embedded light source and receiver could be used in many different scenarios including a) left in place in various rivers, bays, hot tubs, rainwater collectors to provide ongoing information regarding levels of pollution/dirtiness/toxins in the water, and/or b) in a deep sea drone or other autonomous underwater device to obtain either continuous or serial assessments of water contents to map the flow of currents or other contents or objects in the ocean in order to calculate the direction of and to follow the object that generated those substances.

Figure 10:
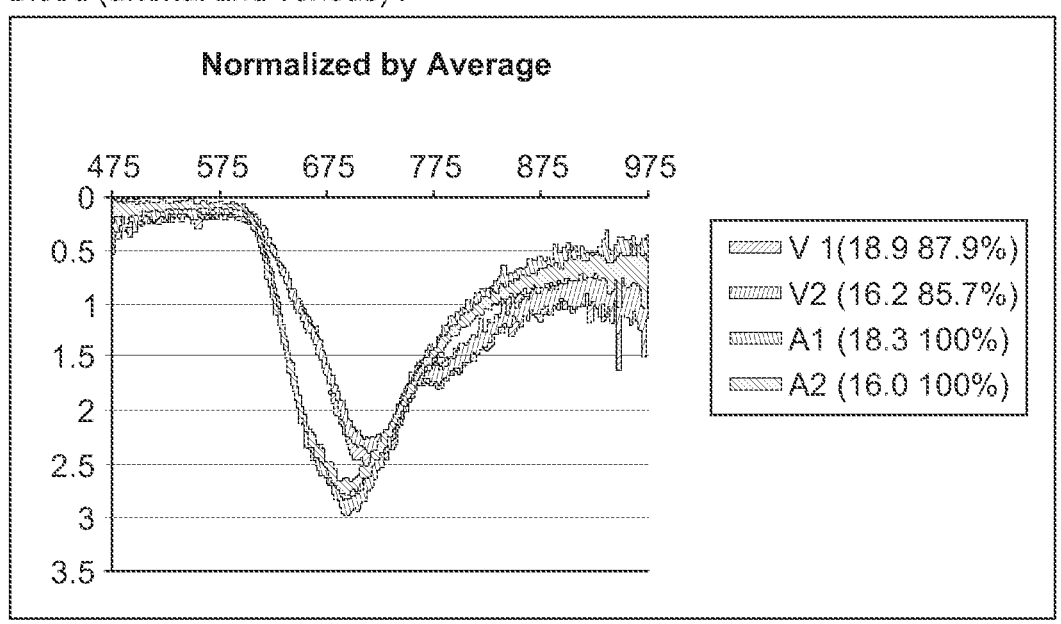
FIG. 10 is another graph of an optical transmission spectrum through a catheter containing arterial and venous blood from a patient.

In another use, an ecologic drone may float on or in a body of water periodically drawing water through a tube for detection of toxic algae; in such a case, the algal concentration and toxin concentration in the water may be estimated if the path length of light through the samples remains fixed. In particular, a point-of-use method for monitoring at least one parameter of a fluid specimen comprises steps to collect sample measurements of a fluid extracted at a point of use, calibrate and normalize signals, and analyze the collected spectrum including the capability (as shown in FIGS. 3 and 10) to display the results to a user at the point of use.

Indeed, in one embodiment of the invention, the catheter device described above can physically connect (or Bluetooth-connect) to a personal smartphone app (or have its own microprocessor and display) that either 1) has software loaded onto it or is linked to a cloud-based analysis platform or 2) bypasses smartphone use by directly processing its collected information or sending that information into a cloud-based platform for analysis. In either case, the analysis results can be returned to the display of the device or to some other notification mechanism (e.g., text message to a smartphone).

Figure 7:
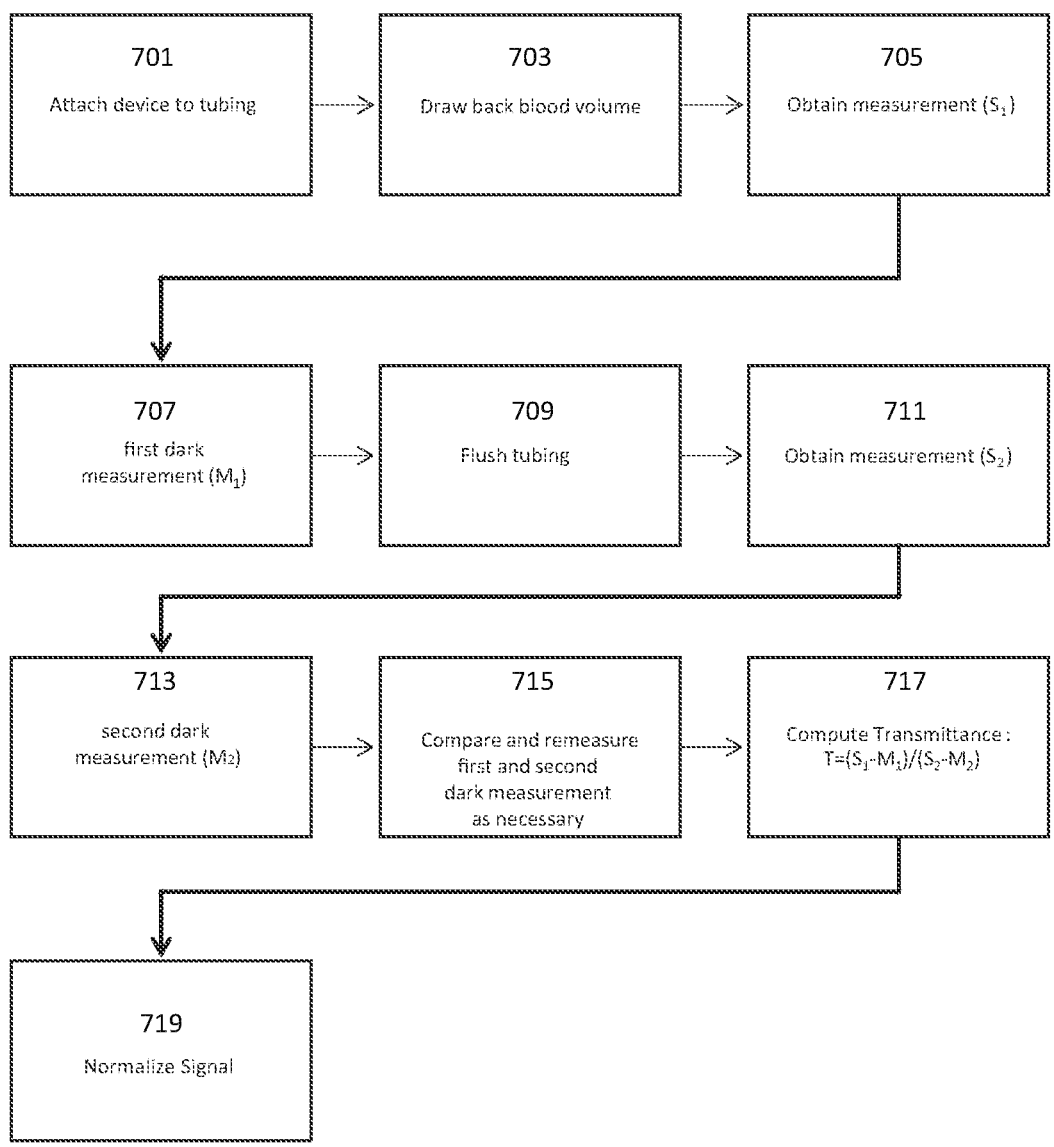
FIG. 7 is a flow chart depicting one method of the present invention for using the devices described above.

Referring now to FIG. 7, what is shown is a flowchart depicting a sequence of steps for monitoring at least one parameter of a fluid specimen, in this preferred embodiment from a patient. Specifically, the steps depicted are:

Attaching a device 10 comprising an optical analyzer to tubing, at a particular distance from a specimen injection port (701); drawing back blood volume (volume determined by measurement, e.g., ~5 ml) (703); obtaining a first specimen measurement ($S_1$, attenuated by blood and tubing) (705); obtaining a first dark measurement ($M_1$, with closed shutter) (707); flushing blood from the tubing using fluid (e.g., saline) until visibly clear (709); obtaining a second specimen measurement ($S_2$, attenuated by tubing and saline, approx. equal to transparent) (711); Obtaining a second dark measurement ($M_2$, with closed shutter) (713); and comparing the dark measurements ($M_1$ to $M_2$) (715).

If M1 and M2 differ by more than some percent threshold amount or other metric to assess variation across the spectrum, this suggests the amount of ambient light is changing significantly during or between the measurements. In the event of such an error, the measurements should be repeated as necessary after reducing ambient light exposure using techniques including blocking the sampling region with light-proof material. An alternative to re-measuring would be to correct using chopped pseudo-random calculation. Then, using the measurements, the next step is computing transmittance (717), according to the following formula for the ratio of the differences between the sample and dark measurements, where S and M are vectors (arrays of numbers); vector subtraction is per usual math definition, and division is index-by-index as in:

$$T[\lambda] = (S_1[\lambda] - M_1[\lambda])/(S_2[\lambda] - M_2[\lambda]) \text{ for each lambda } \lambda,$$

where lambda $\lambda$ is the center wavelength of each sample from spectrometer After computing the transmittance is a step of scaling and fitting the data to known spectra target values or otherwise normalizing or performing other processing of the raw transmission data (719). If the light path distance through the sample material is known, one can determine an absolute attenuation per unit length and thus provide an estimate the concentration of a substance with a known spectral profile. If the distance is variable, the pattern of light attenuation at different wavelengths can still be analyzed much as modern audio and video signal processors analyze patterns of signals rather than absolute measurements of physical quantities, whether light intensity reaching a video camera or sound pressure arriving at a microphone.

Figure 9:
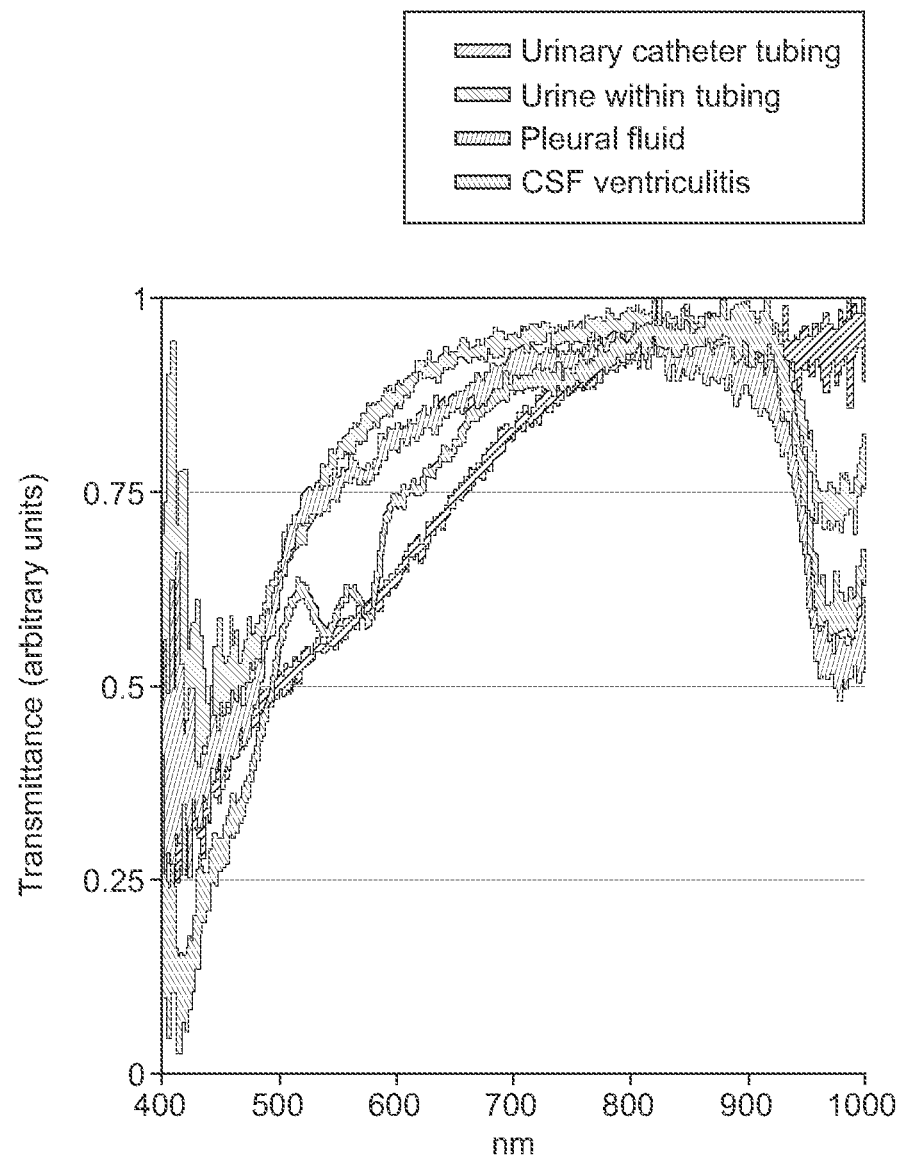
FIG. 9 is a graph of an optical transmission spectrum through a catheter containing body fluids, including urine, pleural fluid, and cerebrospinal fluid from a patient.

FIG. 9 is a graph of an optical transmission spectrum through a catheter containing body fluids, including urine, pleural fluid, and cerebrospinal fluid from a patient using the steps described above. FIG. 10 is another graph of an optical transmission spectrum through a catheter containing arterial and venous blood from a patient using the steps described above.

Generalized Statements of the Invention

The following are generalized numbered statements of the invention describing different aspects of this invention. These statements are provided for illustrative purposes.

1. A device for monitoring at least one parameter of a fluid specimen (obtained for example from a patient), comprising: a fluid conduit holder comprising a clamp configured to position a fluid conduit, which holds the fluid specimen-obtained from the patient, in a position for optical analysis; an optical analyzer comprising a light source and a light detector, the optical analyzer configured to expose the fluid specimen contained within the fluid conduit to an illuminant and measure light (e.g., a spectrum or an absorption or a transmission or an emission of light from the fluid specimen) received at the detector; and an optical alignment mechanism mechanically coupling the light source, the clamp, and the light detector together, and configured to align at least the light detector with the fluid conduit at the position for optical analysis. While denoted in this statement with respect to a fluid specimen obtained for example from a patient, the present invention is not so limited and can be used for point-of-use spectroscopic analysis of any fluids.

2. The device of statement 1, further comprising: an access device configured to receive the fluid specimen from the patient (or other source) with the fluid conduit comprising a space contiguous with a body of the patient, wherein the fluid conduit comprises tubing attached to indwelling arterial or venous catheters or to an indwelling catheter in a compartment of the body of the patient, and the tubing is configured to hold the fluid specimen in place for the optical analyzer.

3. The device of any of the statements above, wherein the incident light travels through walls of the tubing, resulting in absorption of the light by contents of the tubing.

4. The device of any of the statements above, wherein the optical analyzer is configured to obtain and compare multiple spectral profiles of the light transmitted through the tubing.

5. The device of any of the statements above, wherein the optical analyzer is configured to provide a high-resolution spectral transmittance profile over a broad wavelength range from 300 nm to 1000 nm.

6. The device of any of the statements above, wherein the optical alignment mechanism comprises an elongated alignment rail comprising a proximal end and a distal end, and wherein the light detector is located proximate to the proximal end, and the light source is located proximate to the distal end.

7. The device of any of the statements above, wherein the optical alignment mechanism comprises a moveable block to locate the fluid conduit at a position of alignment with the light.

8. The device of any of the statements above, wherein the fluid conduit holder comprises a conduit retainer configured to position the fluid conduit at the position of alignment.

9. The device of statement 8, wherein the conduit retainer is configured to position the fluid conduit at the position of alignment without the incident light passing through any airspace or gap.

10. The device of statement 8, wherein the conduit retainer comprises at least one jaw configured to position the fluid conduit at the position of alignment.

11. The device of statement 8, wherein the at least one jaw is configured to clamp and retain the fluid conduit.

12. The device of any of the statements above, wherein the optical alignment mechanism comprises a rail and at least one moveable block having dovetails attached to the rail.

13. The device of statement 12, wherein the rail and the dovetails are configured to place in alignment a) the light source, b) the fluid conduit, and c) the light detector.

14. The device of any of the statements above, wherein the fluid conduit comprising a tube, and the optical alignment mechanism further comprises a tube alignment channel and tube retainer which secures the tube.

15. The device of any of the statements above, wherein the tube retainer secures the tube into the channel.

16. The device of any of the statements above, wherein the incident light comprises a source emitting light from 300 nm to 1000 nm for optical absorption analysis of components in the fluid specimen.

17. The device of any of the statements above, wherein the incident light comprises a light emitting diode emitting light for optical absorption analysis of components in the fluid specimen.

18. The device of any of the statements above, wherein the incident light source comprises a light emitting diode emitting ultraviolet light for fluorescence analysis of components in the fluid specimen.

19. A hand-held device for monitoring at least one parameter of a fluid specimen obtained from a patient, comprising: a fluid conduit holder configured to position a fluid conduit, which holds the fluid specimen-obtained from the patient, in a position for optical analysis; an optical analyzer comprising a light source and a light detector, the optical analyzer configured to expose the fluid specimen contained within the fluid conduit to an illuminant and measure light (e.g., a spectrum or an absorption or a transmission or an emission of light from the fluid specimen) received at the detector; and an optical alignment mechanism configured to clamp the fluid conduit at the position for optical analysis.

20. A method for monitoring at least one parameter of a fluid specimen (obtained for example from a patient), comprising: receiving the fluid specimen into the device of any one or more of statements 1-19; exposing the fluid specimen to incident light; measuring light (e.g., a spectrum or an absorption or a transmission or an emission of light from the fluid specimen) received at a detector in alignment with the fluid specimen; and storing data of the measured light for analysis.

21. The method of statement 20, wherein measuring comprises: attaching the device of any one or more of statements 1-19 comprising an optical analyzer to tubing, at a designated distance from a specimen injection port; drawing blood or another volume of a fluid specimen into the tubing, obtaining a first specimen measurement S1 where incident light is attenuated by blood (or the other fluid); obtaining a first dark measurement (for example with a closed shutter or the light source off); flushing the blood (or other fluid) from the tubing using a second fluid (e.g., saline) until clear of the blood; obtaining a second specimen S2 measurement where the incident light is attenuated by tubing and saline; obtaining a second dark measurement M2; and optionally comparing the dark measurements (M1 to M2).

22. The method of statement 20 or statement 21, further comprising computing a transmittance spectrum for the fluid specimen.

23. The method of statement 22, where the transmittance spectrum is calculated according to the following formula determining a ratio of differences between the sample and dark measurements:

$$T = \frac{(S_1 - M_1)}{(S_2 - M_2)}$$

24. The method of statement 22 or statement 23, further comprising scaling and/or fitting data for the transmittance spectrum to spectra target values.

25. A computer readable medium which when executed by a processor performs any of the following, comprising: monitoring at least one parameter of a fluid specimen (obtained for example from a patient), received into the device of any one or more of statements 1-19; exposing the fluid specimen to incident light; measuring light measure light (e.g., a spectrum or an absorption or a transmission or an emission of light from the fluid specimen) received at a detector in alignment with the fluid specimen; and storing data of the measured light for analysis.

26. The computer readable medium of statement 25, wherein the processor is programmed to: obtain a first specimen measurement S1 where incident light is attenuated by blood (or the other fluid) drawn into a tubing optically aligned with the device of any one or more of statements 1-19; obtaining a first dark measurement (for example with a closed shutter or the light source off); obtaining a second specimen S2 measurement where incident light is attenuated by tubing and a flushing fluid used to clear the tube of the fluid specimen; obtaining a second dark measurement M2; and comparing the dark measurements (M1 to M2); and optionally comparing the dark measurements (M1 to M2).

27. The computer readable medium of statement 25 or statement 26, further comprising computing a transmittance spectrum for the fluid specimen.

28. The computer readable medium of statement 27, where the transmittance spectrum is calculated according to the following formula determining a ratio of differences between the sample and dark measurements:

$$T = \frac{(S_1 - M_1)}{(S_2 - M_2)}$$

29. The computer readable medium of statement 27 or statement 28, further comprising scaling and/or fitting data for the transmittance spectrum to spectra target values.

Numerous modifications and variations of the invention are possible in light of the above teachings. It is therefore to be understood that within the scope of the appended claims, the invention may be practiced otherwise than as specifically described herein.

The invention claimed is:

1. A device for monitoring at least one parameter of a fluid specimen obtained from a patient, comprising:
a fluid conduit holder comprising a conduit retainer configured to position a fluid conduit, which holds the fluid specimen obtained from the patient, in a position for optical analysis;
an optical analyzer comprising a light source and a light detector, the optical analyzer configured to expose the fluid specimen contained within the fluid conduit to an illuminant and measure light received at the detector; and
an optical alignment mechanism mechanically coupling the light source, the conduit retainer, and the light detector together, and configured to align at least the light detector with the fluid conduit at the position for optical analysis, wherein the conduit retainer is configured to position the fluid conduit at a position of alignment with the light, without incident light passing through any airspace or gap.

2. The device of claim 1, further comprising:

an access device configured to receive the fluid specimen from the patient with the fluid conduit comprising a space contiguous with a body of the patient, wherein the fluid conduit comprises tubing attached to indwelling arterial or venous catheters or to an indwelling catheter in a compartment of the body of the patient, and the tubing is configured to hold the fluid specimen in place for the optical analyzer.

3. The device of claim 2, wherein the incident light travels through walls of the tubing, resulting in absorption of the light by contents of the tubing.

4. The device of claim 2, wherein the optical analyzer is configured to obtain and compare multiple spectral profiles of the light transmitted through the tubing.

5. The device of claim 1, wherein the optical analyzer is configured to provide a high-resolution spectral transmittance profile over a broad wavelength range from 300 nm to 1000 nm.

6. The device of claim 1, wherein the optical alignment mechanism comprises an elongated alignment rail comprising a proximal end and a distal end, and wherein the light detector is located proximate to the proximal end, and the light source is located proximate to the distal end.

7. The device of claim 1, wherein the optical alignment mechanism comprises a moveable block to locate the fluid conduit at the position of alignment with the light.

8. The device of claim 1, wherein the conduit retainer comprises at least one jaw configured to position the fluid conduit at the position of alignment.

9. The device of claim 8, wherein the at least one jaw is configured to clamp and retain the fluid conduit.

10. The device of claim 8, wherein the at least one jaw comprises semi-rigid or moldable material.

11. The device of claim 8, wherein the at least one jaw has a substantially semi-circular shape that fits the fluid conduit.

12. The device of claim 1, wherein the optical alignment mechanism comprises a rail and at least one moveable block having dovetails attached to the rail.

13. The device of claim 12, wherein the rail and the dovetails are configured to place in alignment a) the light source, b) the fluid conduit, and c) the light detector.

14. The device of claim 1, wherein the fluid conduit comprises a tube, and the optical alignment mechanism further comprises a tube alignment channel and tube retainer which secures the tube.

15. The device of claim 14, wherein the tube retainer secures the tube into the channel.

16. The device of claim 1, wherein the light source comprises a source emitting light from 300 nm to 1000 nm for optical absorption analysis of components in the fluid specimen.

17. The device of claim 1, wherein the light source comprises a light emitting diode emitting light for optical absorption analysis of components in the fluid specimen.

18. The device of claim 1, wherein the light source comprises a light emitting diode emitting ultraviolet light for fluorescence analysis of components in the fluid specimen.

19. A method for monitoring at least one parameter of a fluid specimen obtained from a patient, comprising:

receiving the fluid specimen into the device of claim 1;

exposing the fluid specimen to incident light;

measuring light at a detector in alignment with the fluid specimen; and storing data of the measured light for analysis.

20. A hand-held device for monitoring at least one parameter of a fluid specimen obtained from a patient, comprising:

a fluid conduit holder comprising a conduit retainer configured to position a fluid conduit which holds the fluid specimen-obtained from the patient in a position for optical analysis;

an optical analyzer comprising a light source and a light detector, the optical analyzer configured to expose the fluid specimen to incident light and measure light received at the light detector; and an optical alignment mechanism configured to clamp the fluid conduit in the conduit retainer at the position for optical analysis, wherein the conduit retainer is configured to position the fluid conduit at a position of alignment with the light, without incident light passing through any airspace or gap.

* * * * *